United States Patent
Britton et al.

(10) Patent No.: US 10,966,788 B2
(45) Date of Patent: *Apr. 6, 2021

(54) SENSOR-BASED SHOULDER SYSTEM AND METHOD

(71) Applicant: Zimmer, Inc., Warsaw, IN (US)

(72) Inventors: Orsa Britton, Warsaw, IN (US); David A. Nolan, Fort Wayne, IN (US); William Van Kampen, Saline, MI (US)

(73) Assignee: Zimmer, Inc., Warsaw, IN (US)

( * ) Notice: Subject to any disclaimer, the term of this patent is extended or adjusted under 35 U.S.C. 154(b) by 23 days.

This patent is subject to a terminal disclaimer.

(21) Appl. No.: 16/219,512

(22) Filed: Dec. 13, 2018

(65) Prior Publication Data

US 2019/0117312 A1    Apr. 25, 2019

Related U.S. Application Data

(63) Continuation of application No. 15/204,590, filed on Jul. 7, 2016, now Pat. No. 10,188,464.

(Continued)

(51) Int. Cl.
*A61B 5/00* (2006.01)
*A61F 2/40* (2006.01)
(Continued)

(52) U.S. Cl.
CPC ............ *A61B 34/10* (2016.02); *A61B 5/4528* (2013.01); *A61B 5/4576* (2013.01);
(Continued)

(58) Field of Classification Search
CPC ..... A61B 5/4528; A61B 5/4576; A61B 5/458; A61B 5/4585; A61B 5/4566; A61F 2/40;
(Continued)

(56) References Cited

U.S. PATENT DOCUMENTS

| 5,456,724 A | 10/1995 | Yen et al. |
| 5,470,354 A | 11/1995 | Hershberger et al. |

(Continued)

FOREIGN PATENT DOCUMENTS

| CN | 103945763 | 7/2014 |
| CN | 104244860 | 12/2014 |

(Continued)

OTHER PUBLICATIONS

"Chinese Application Serial No. 201680051775.9, Office Action dated Apr. 3, 2019", w English translation, 17 pgs.

(Continued)

*Primary Examiner* — Brian A Dukert
(74) *Attorney, Agent, or Firm* — Schwegman Lundberg & Woessner, P.A.

(57) ABSTRACT

The subject matter includes a system and method for providing graphical feedback visualizing forces within a joint through a range of motion of the joint. The method can comprise receiving position data, receiving force data, and generating a graphical representation based on the position data and the force data. The receiving position data can include data for at least one bone of a joint while the at least one bone is moved through a range of motion (ROM). The receiving force data can occur concurrently to receiving the position data and using one or more processors, the force data can be collected from at least one force sensor embedded within a trial prosthesis in the joint. The graphical representation can illustrate changes in the force data versus locations of the bone as it moved through the ROM.

22 Claims, 15 Drawing Sheets

Related U.S. Application Data

(60) Provisional application No. 62/190,054, filed on Jul. 8, 2015.

(51) Int. Cl.
  A61B 34/10 (2016.01)
  A61F 2/46 (2006.01)
  A61F 2/30 (2006.01)

(52) U.S. Cl.
  CPC .......... *A61F 2/4014* (2013.01); *A61F 2/4081* (2013.01); *A61F 2/4657* (2013.01); *A61F 2/4684* (2013.01); *A61B 2034/105* (2016.02); *A61B 2034/107* (2016.02); *A61F 2/40* (2013.01); *A61F 2002/3037* (2013.01); *A61F 2002/30566* (2013.01); *A61F 2002/30616* (2013.01); *A61F 2002/30672* (2013.01); *A61F 2002/4633* (2013.01); *A61F 2002/4666* (2013.01); *A61F 2002/4668* (2013.01)

(58) Field of Classification Search
  CPC .... A61F 2/4014; A61F 2/4081; A61F 2/4657; A61F 2/4684; A61F 2002/3037; A61F 2002/30566; A61F 2002/4633; A61F 2002/4666
  See application file for complete search history.

(56) References Cited

U.S. PATENT DOCUMENTS

| | | | |
|---|---|---|---|
| 5,961,474 | A | 10/1999 | Reis |
| 7,175,663 | B1 | 2/2007 | Stone |
| 10,188,464 | B2 | 1/2019 | Britton et al. |
| 2004/0019384 | A1 | 1/2004 | Kirking et al. |
| 2004/0113790 | A1 | 6/2004 | Hamel et al. |
| 2004/0243148 | A1 | 12/2004 | Wasielewski |
| 2005/0000104 | A1* | 1/2005 | Arnin ............ A61B 5/1077 33/555.1 |
| 2009/0247863 | A1 | 10/2009 | Proulx et al. |
| 2010/0249533 | A1 | 9/2010 | Pierce et al. |
| 2010/0331682 | A1 | 12/2010 | Stein et al. |
| 2011/0218458 | A1 | 9/2011 | Valin et al. |
| 2012/0029389 | A1 | 2/2012 | Amiot et al. |
| 2013/0226034 | A1 | 8/2013 | Stein et al. |
| 2013/0261503 | A1 | 10/2013 | Sherman |
| 2014/0200584 | A1 | 7/2014 | Stein et al. |
| 2017/0007330 | A1 | 1/2017 | Britton et al. |

FOREIGN PATENT DOCUMENTS

| | | |
|---|---|---|
| CN | 108289743 A | 7/2018 |
| EP | 2229883 A1 | 9/2010 |
| EP | 2644166 A1 | 10/2013 |
| JP | 2008526427 A | 7/2008 |
| JP | 2013212379 A | 10/2013 |
| JP | 2018530358 A | 10/2018 |
| WO | 2007126917 | 11/2007 |
| WO | 2013044157 | 3/2013 |
| WO | WO-2014071193 A1 | 5/2014 |
| WO | 2014144107 | 9/2014 |
| WO | WO-2014149079 A1 | 9/2014 |
| WO | WO-2017007929 A1 | 1/2017 |

OTHER PUBLICATIONS

"U.S. Appl. No. 15/204,590, Corrected Notice of Allowability dated Oct. 23, 2018", 3 pgs.
"U.S. Appl. No. 15/204,590, Non Final Office Action dated Apr. 30, 2018", 10 pgs.
"U.S. Appl. No. 15/204,590, Notice of Allowance dated Sep. 14, 2018", 5 pgs.
"U.S. Appl. No. 15/204,590, Response filed Feb. 12, 2018 to Restriction Requirement dated Dec. 14, 2017", 6 pgs.
"U.S. Appl. No. 15/204,590, Response Filed Jul. 13, 2018 to Non-Final Office Action dated Apr. 30, 2018", 7 pgs.
"U.S. Appl. No. 15/204,590, Restriction Requirement dated Dec. 14, 2017", 6 pgs.
"International Application Serial No. PCT/US2016/041326, International Search Report dated Oct. 10, 2016", 5 pgs.
"International Application Serial No. PCT/US2016/041326, Written Opinion dated Oct. 10, 2016", 7 pgs.
"European Application Serial No. 16741467.1, Response filed Sep. 21, 2018 to Office Action dated Mar. 16, 2018", 51 pgs.
"International Application Serial No. PCT/US2016/041326, International Preliminary Report on Patentability dated Jan. 18, 2018", 9 pgs.
"Australian Application Serial No. 2016291149, First Examination Report dated Jul. 31, 2019", 3 pgs.
"Australian Application Serial No. 2016291149, Response filed Sep. 19, 2019 to First Examination Report dated Jul. 31, 2019", 16 pgs.
"Canadian Application Serial No. 2,991,495, Office Action dated Aug. 14, 2019", 5 pgs.
"Canadian Application Serial No. 2,991,495, Response filed Feb. 14, 2020 to Office Action dated Aug. 14, 2019", 10 pgs.
"Chinese Application Serial No. 201680051775.9, Office Action dated Nov. 4, 2019", (w/English Translation), 9 pgs.
"Chinese Application Serial No. 201680051775.9, Response filed Jan. 8, 2020 Office Action dated Nov. 4, 2019", w/ English claims, 11 pgs.
"Chinese Application Serial No. 201680051775.9, Response filed Jul. 22, 2019 to Office Action dated Apr. 3, 2019", w/ English claims, 11 pgs.
"Japanese Application Serial No. 2018-500444, Notification of Reasons for Refusal dated Aug. 20, 2019", w/ English translation, 12 pgs.
"Japanese Application Serial No. 2018-500444, Office Action dated Mar. 3, 2020", w/ English translation, 9 pgs.
"Japanese Application Serial No. 2018-500444, Response filed Nov. 22, 2019 to Notification of Reasons for Refusal dated Aug. 20, 2019", w/ English claims, 8 pgs.
"Japanese Application Serial No. 2018-500444, Notification of Reasons for Refusal dated Aug. 4, 2020", with English translation, 4 pages.
"European Application Serial No. 20151841.2, Extended European Search Report dated Jan. 26, 2021", 8 pgs.

* cited by examiner

SENSOR-BASED SHOULDER SYSTEM AND METHOD

CLAIM OF PRIORITY

This application is a continuation of U.S. patent application Ser. No. 15/204,590, filed on Jul. 7, 2016, which claims the benefit of U.S. Provisional Patent Application Ser. No. 62/190,054, filed on Jul. 8, 2015, the benefit of priority of each of which is claimed hereby, and each of which is incorporated by reference herein in its entirety.

BACKGROUND

The shoulder joint is a complex joint with the scapula, clavicle and the humerus all coming together to enable a wide range of movement, at least in a properly functioning joint. In a properly functioning shoulder joint the head of the humerus fits into a shallow socket in the scapula, typically referred to as the glenoid. Articulation of the shoulder joint involves movement of the humeral head in the glenoid, with the structure of the mating surfaces and surrounding tissues providing a wide range of motion.

The shoulder joint can undergo degenerative changes caused by various issues, such as rheumatoid arthritis, osteoarthritis, rotator cuff arthroplasty, vascular necrosis or bone fracture. When severe joint damage occurs and no other means of treatment is found to be effective, a total, partial, or reverse shoulder replacement or reconstruction may be necessary. Total shoulder replacements can involve a humeral prosthetic, including a stem and a head portion used to replace the natural humeral head. Total shoulder replacements will also typically involve resurfacing of the glenoid with a prosthetic implant. The glenoid implant generally will include an articulating cup shaped to receive the prosthetic humeral head. A reversal shoulder replacement (arthroplasty) involves a different set of humeral and glenoid replacement prosthetics. In a reverse shoulder the humeral component includes a cup shaped articular surface attached to a stem implanted into the humerus, while a spherical glenoid component is used to provide an articular surface for the humeral cup.

During shoulder arthroplasty surgery, the components of the prosthesis are matched with the bio-kinematics of the patient in an effort to maintain or restore a natural range of motion of a healthy shoulder joint. Patient specific instrumentation, such as Zimmer PSI (add reference), can assist a surgeon in planning and implementing a shoulder arthroplasty to restore natural bio-kinematics. However, even with the multitude of advances in prosthetic components and patient specific instrumentation, restoring a full range of motion can remain difficult, especially for a surgeon who does not regularly perform shoulder replacements.

Even current surgical standards are often vague, providing guidance such as joint tension should be 50/50 laxity or the joint should be "stable" throughout the range of motion. It is common for the current surgical standards to use un-quantified subject measures, such as if the fit is "too tight" perform any necessary soft tissue releases. Without significant experience, such guidance is of little practical use in ensuring successful outcomes.

While the above discusses issues and procedures specific to shoulder replacement procedures, discussion of the following systems, devices, methods, and instruments is also applicable for use in other joint replacement procedures, such as total hip arthroplasty (THA) or total knee arthroplasty (TKA).

OVERVIEW

The systems and methods discussed herein may utilize technologies similar to those described in the following references. A system or device for tracking bone position during movement through a range of motion, such as the those discussed in U.S. Patent Publication 2011/0218458, titled "MEMS-BASED METHOD AND SYSTEM FOR TRACKING A FEMORAL FRAME OF REFERENCE," U.S. Pat. No. 5,961,474, titled "NON-INVASIVE MEASUREMENT OF JOINT TRANSLATION AND RANGE OF MOTION," U.S. Patent Publication 2012/0029389, titled "BONE TRACKING WITH A GYROSCOPE SENSOR IN COMPUTER-ASSISTED SURGERY," or U.S. Patent Publication 2009/0247863, titled "TRACKING SYSTEM AND METHOD." Integration of force sensor technology into trial prosthetic devices to provide quantitative feedback during joint procedures, such as those discussed in U.S. Patent Publication 2010/0331682, titled "DEVICE AND METHOD FOR ADVANCED LOW-POWER MANAGEMENT OF A SENSOR TO MEASURE A PARAMETER OF THE MUSCULAR-SKELETAL SYSTEM."

Evidence-based medicine continues to gain in popularity as a method to quantify patient outcomes and benefits of certain procedures. The systems and methods discussed herein build on evidence-based medicine collection systems such as the one discussed in U.S. Patent Publication 2010/0249533, titled "SYSTEM AND METHOD FOR AN ORTHOPEDIC DATA REPOSITORY AND REGISTRY."

The present inventors have recognized, among other things, that a problem to be solved can include determining a proper understanding of joint tensioning and range of motion during a total shoulder or reverse shoulder replacement, resulting in proper prosthesis size selection or other surgical technique usage (e.g., soft tissue releases). The systems and methods discussed herein can assist in providing a solution to this problem by using various quantitative analyses of joint function (this includes joint tensioning and a quantitative mapping of joint range of motion) before and/or during a procedure. The present inventors have also recognized, among other things, that a problem to be solved can also include providing quantitative evidence of improved joint function post-procedure. The systems and methods discussed herein can help provide a solution to this problem, such as by graphically depicting pre-operative and post-operative range of motion, as well as providing a graphical indication (mapping) of improvement in range of motion, among other things. Yet further, the present inventors have recognized, among other things, that a problem to be solved can include accurately sensing joint forces within a shoulder joint throughout the total range of motion. The systems, devices, and methods discussed herein provide a solution to this problem, such as by using one of various trial prostheses with integrated force sensor technology.

The present inventors have recognized that the availability of compact sensor technology and miniaturized electronic circuitry (e.g., for wireless communication) enables new, clinically relevant information to be gathered and brought to bear within the operating theatre, which presents the opportunity to assist surgeons in performing successful operations. In particular, additional quantitative data and feedback during a procedure, when compared to known standards (e.g., standards developed using methods and apparatus discussed herein) developed based on successful outcomes, can assist in guiding both veteran and novice surgeons towards similarly successful outcomes. By way of example, the following uses total shoulder replacements as an exemplary joint replacement procedure to discuss the disclosed systems, devices, instruments, and methods.

The basic system discussed in some examples herein comprises a force sensing device(s), a position sensing device, and a graphical user interface generated by a computer communicatively coupled to the various sensors. In some examples, the system can further include strain gauges or other similar additional inputs providing additional information about the bones and soft tissue surrounding the target joint.

In an example, force-sensing devices can be placed in the shoulder joint on the humeral side and/or on the glenoid side to assess joint tension. The sensors can be inserted into a humeral (liner) space tray trial or in a glenosphere trial in a reverse shoulder arthroplasty (RSA) procedure (see FIG. 1). In a total shoulder arthroplasty (TSA) procedure, the force sensors can be inserted into a humeral head trial or a glenoid trial implant (see FIG. 2). In another example, force-sensing technology is incorporated into monoblock trial stem that has a head/stem construct mated together with the sensor in the trial head (FIG. 13). Trial prostheses can be specially designed to contain one or more force sensing devices that provide quantitative feedback regarding tension within the prosthetic joint components. In certain examples, the surgical kit includes multiple trial sizes with each different size including force sensing devices or the surgical kit can include interchangeable force sensor modules used with different trial sizes as necessary. Sensor technology can be adapted to various different form-factors of prostheses, such as stemmed, stemless, and monoblock, among others. As discussed below in greater detail, using force sensors to provide quantitative feedback can assist the surgeon in selecting the proper prosthesis size and in balancing soft tissue within the joint prior to final implantation. A key to a successful outcome in joint replacement procedures is getting the boney anatomy and the soft tissue balancing correct, where the prosthesis selection affects aspects of both and additional procedures (e.g., soft tissue release) complete the process.

A position-sensing device can be attached to a limb (or another instrument) associated with the target joint to track movement of the limb through a range of motion. In an example, the position-sensing device can be attached to an arm, and the patient's arm can then be moved through a range of movements. The range of motion (ROM) can include positions such as elevation, adduction, abduction, flexion and extension, internal and external rotation, as well as practical arm positions such as "brush your teeth" or "lift yourself from a chair." In an example, the position-sensing pod contains accelerometers, gyroscopes, or other similar position sensors that can determine the movements of the arm and report position (or relative positions), which can then be correlated to force sensor data received concurrently.

In an example, a computing device receives signals from the force sensors and position-sensing device and analyzes the date to provide quantitative feedback to the surgeon. For example, the computing device can correlate force sensor data with the position information to generate a "heat map" of joint tension throughout a range of motion (see e.g., FIG. 5). The joint tension data can be mapped out to the various joint positions in any number of ways, such as numerically, topographically using iso-pressure contours, or with color representing the tension (similar to thermal imaging/heat maps).

In some embodiments additional sensors, such as strain gauges, can be used to provide additional information about the bones or soft-tissue surrounding the target joint. In an example, strain gauges can be attached to the soft tissue at various points around the shoulder joint, such as the deltoid, pectoral, latissimus, or triceps. The strain gauge information can be received by the computing device and correlated with the position data or tension information. The computing device can then produce additional or updated numeric or graphical output including strain gauge information. Discussion of the system related to FIG. 8A includes additional details on integration of strain gauge information. With the optional strain gauge sensors, the system can inform the surgeon if particular muscles were being activated in various specific positions or during specific movements, and whether additional soft tissue releases or other tensioning changes (e.g. bigger humeral heads, poly liner thickness changes, humeral and/or glenoid spacers, and even re-cutting the humerus) would be warranted.

A benefit to the surgeon of the systems and methods discussed herein is have an objective and quantified visual feedback of how the joint in its current status is responding to the kinetic movement. The surgeon can take this information and have the ability to make adjustments to the aspects of the surgery under his/her control such as soft tissue releases or implant choices such as humeral tray/spacer thickness and glenosphere size in the context of RSA, or humeral head size in the context of TSA. The system can guide the surgeon on joint tension during reduction of the joint to indicate whether the joint (e.g. shoulder) will be too tight or too loose given use of a particular trial prosthesis. The system can also assist in identifying potential points in the range of motion where the reconstructed joint would be unstable, due to insufficient constraining forces, such as when joint tension drops below a threshold amount in a certain location in the range of motion. The system can further provide feedback regarding the likely extent of range of motion that can be achieved to consider whether the joint, as currently reconstructed, would allow the patient to return to various activities, such as movements required for personal hygiene, eating, or mobility. Objective measures of range of motion (ROM) will also impact Physical Therapy considerations. For example, the surgeon can give an incredibly detailed analysis to the PT about post-ROM. This could, in turn, make a difference in how (or maybe if at all) the PT would change his/her therapy approach.

The systems and methods discussed herein can serve a purpose in demonstrating evidence-based outcomes for joint replacement surgeries. For example, the arm position sensor can be used preoperatively and post-operatively to assess the range or movement. The angular and rotational ranges can be assessed in both active (meaning that the patient is able to move through this RUM by themselves) and passive (meaning that the patients joint can be moved through this ROM with assistance). Regions of pain and instability can be displayed on the map as well, through receiving additional feedback from the patient regarding pain or the surgeon regarding instability (see e.g., FIG. 6). During movement of the joint buttons or commands located on or processed by the computer controller or on the sensor pod itself will be used to categorize these regions based on feedback from the patient, the surgeon, or the sensor system.

The system can be integrated with a complimentary preoperative 3D surgical planning software (like Zimmer PSI™ Shoulder Planning software system), which uses preoperative medical imaging (CT or MRI) to digitally simulate movement of the arm through the range of movement. Surgical planning software can predict digitally the resultant impingement-free ROM that would be achieved given various choices given as inputs, such as glenoid and humeral side implants, their size and position. The digital modeling attempts to account for the patient's bony and soft tissue anatomy. Based on the digital analysis, a heat map, or similar quantitative output, could be produced that shows the predicted impingement-free ROM, and this output could drive alternative surgical planning options to be considered or elected to optimize the ROM for this patient. Further, the preoperative and post-operative ROM analysis discussed above could be further compared with the surgical planning software output to provide additional confirmation of anticipated outcome versus actual outcome. After an appropriate study, the quantitative feedback discussed herein could be used to refine surgical planning software and develop standards for use during a procedure as guides to intra-surgical measurements that led to desired post-surgical outcomes. Use of surgical planning software is not required for generation of pre-operative heat maps illustrating pre-operative range of motion, but the surgical planning software can be useful in adding another element to the pre-operative/intra-operative/post-operative comparison capabilities discussed herein.

As illustrated in FIG. 14, results from preoperative planning software can be used intra-operatively to provide real-time feedback, such as a variance map, based on force-sensor and position data. In some examples, the real-time feedback is provided via graphical depictions of differences in the pre-operative planned range-of-motion, joint tension, or instability graph versus actual data collected during surgery using the mechanisms and techniques discussed herein.

Over time, this information can be benchmarked against data collected from experienced surgeons resulting in quantifiable guidance for less experienced surgeons to gain understanding and intraoperative feedback as they are performing an unfamiliar surgical procedure. Making the adjustments during surgery offers the promise of improved outcomes, shorter recovery periods, less revisions, and better functional performance of the reconstructed joint.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The headings provided herein are merely for convenience and do not necessarily affect the scope or meaning of the terms used.

DETAILED DESCRIPTION

Joint replacement procedures, such as shoulder arthroplasty (total or reverse), are complicated involved procedures where experience can make a significant difference in outcomes for a patient. One aspect of joint replacement procedures that can be difficult for less experienced surgeons is in balancing soft tissues within the joint with proper prosthesis selection or tissue releases. Proper joint tension typically results in better range of motion, joint stability, and longevity of the implants, among other things. However, proper joint tension is typically done solely by feel, with the experienced surgeon having developed over time a "feel" for what will end up working well for each particular patient. The systems and methods discussed herein provide an option for surgeons to obtain quantitative feedback regarding joint tension throughout a complete range of motion of the joint during the procedure. Further, quantitative comparisons of pre-operative, intraoperative, and post-operative joint tension and/or range of motion are also made possible. In some examples, standards for joint tension over a joint range of motion can be developed to allow for intraoperative comparison to standards that are known to have resulted in positive outcomes.

Figure 1:
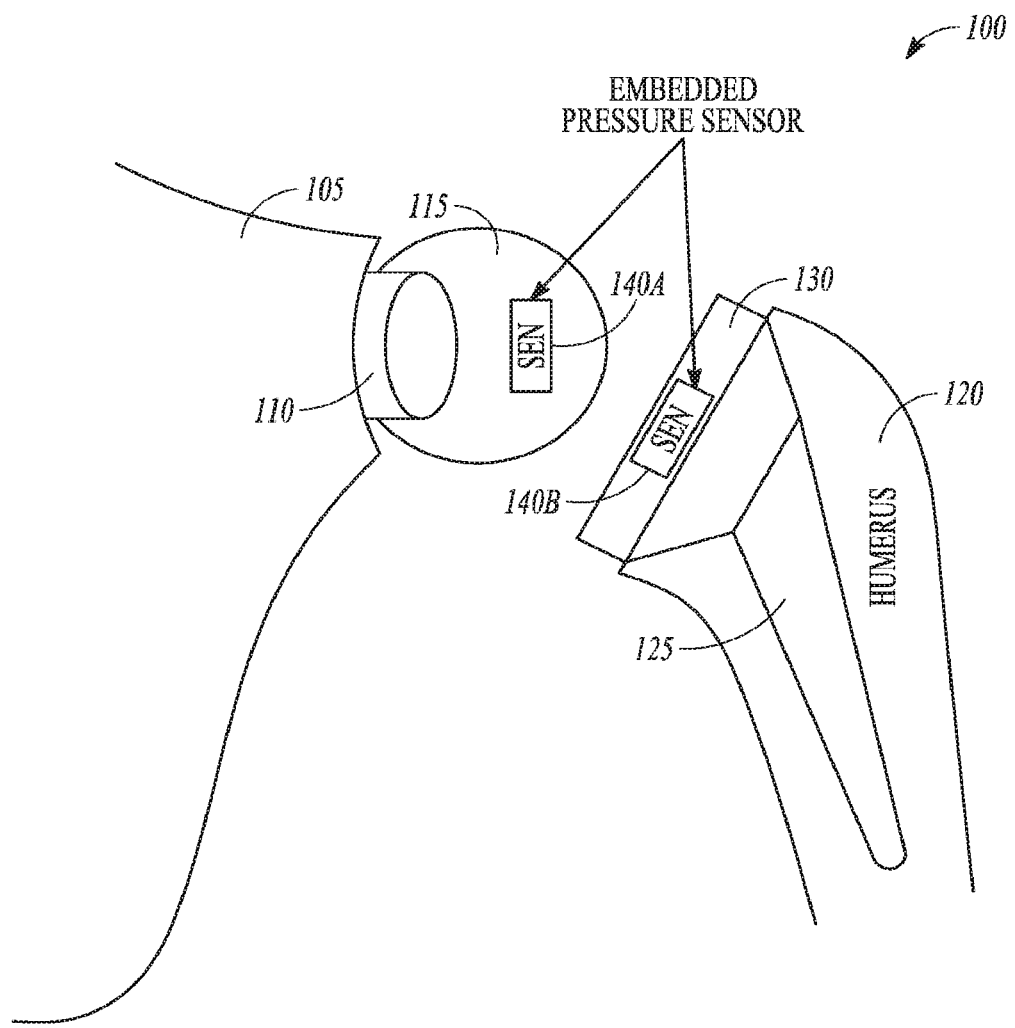
FIG. 1 is a diagram illustrating a reverse shoulder arthroplasty with sensors embedded in trial prostheses, according to some example embodiments.
Figure 3A:
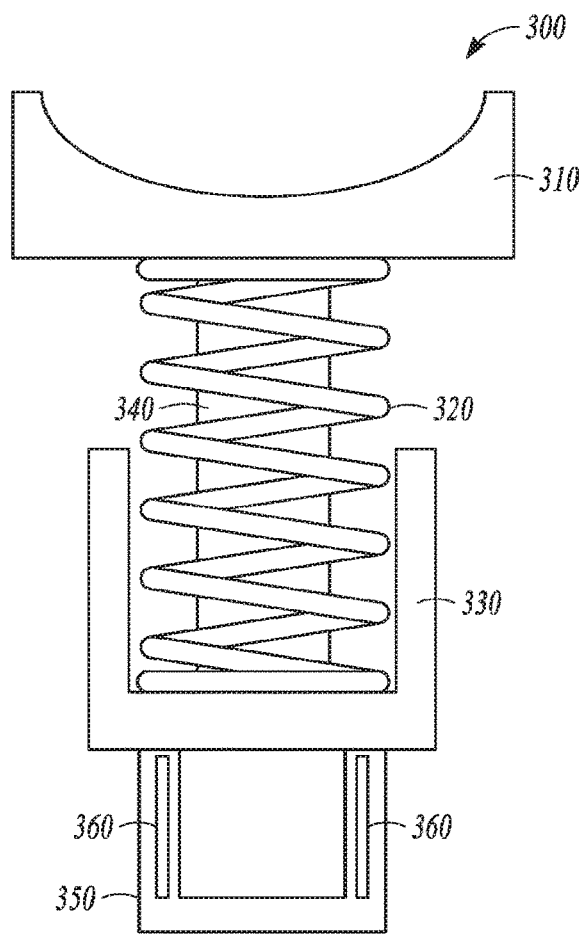
FIG. 3A is a diagram illustrating a force sensor module for use within a trial prosthesis in a low force position, according to some example embodiments.
Figure 3B:
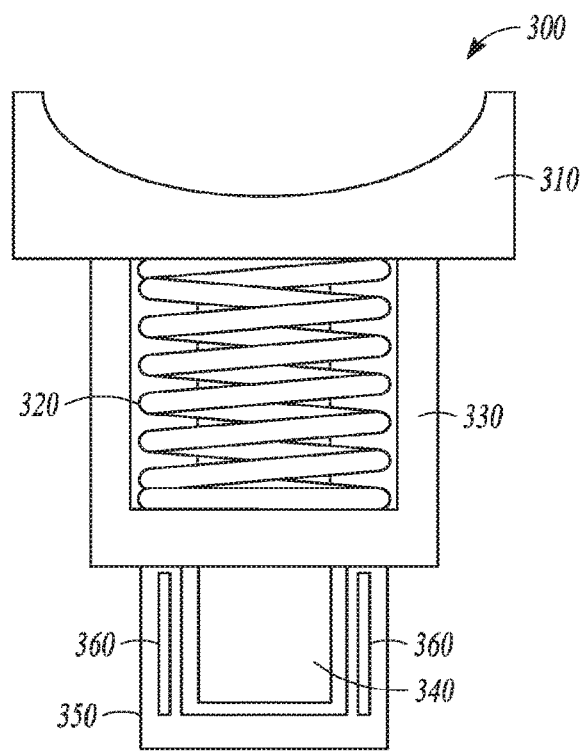
FIG. 3B is a diagram illustrating a force sensor module for use within a trial prosthesis in a high force position, according to some example embodiments.

FIG. 1 is a diagram illustrating a reverse shoulder arthroplasty with sensors embedded in trial prostheses, according to some example embodiments. The reverse shoulder arthroplasty system 100 includes a glenoid prosthesis 110 affixed to the scapula 105 with a glenosphere trial including an embedded force sensor 140A. On the humeral side, the reverse shoulder arthroplasty system 100 includes a humeral prosthesis 125 affixed within the humerus 120 with a humeral tray trial 130 including an embedded force sensor 140B. The embedded force sensors can optionally be encased within the trial or removable modules. In some examples, the force sensors are integral within the trial, such as illustrated in FIGS. 3A and 3B discussed in detail below. In an example, the force sensors, such as embedded force sensors 140A, 140B, communicate force data wirelessly to a computing device, which can then analyze the data to provide feedback to the surgeon. The embedded force sensors 140A, 140B are designed to receive force transmitted between the glenosphere trial 115 and the humeral tray trial 130 when the shoulder is reduced to check joint tension with the trial prostheses in place. In some examples, a single embedded force sensor, such as embedded force sensor 140A, is used to provide accurate force data for the joint. In other examples, multiple force sensors are embedded within different portions of the trial prostheses to provide additional information on loading patterns within the joint. For example, force sensors can be embedded around the periphery of a humeral tray trial, which allows mapping of the force on different portions of the trial throughout the entire range of motion.

Figure 2:
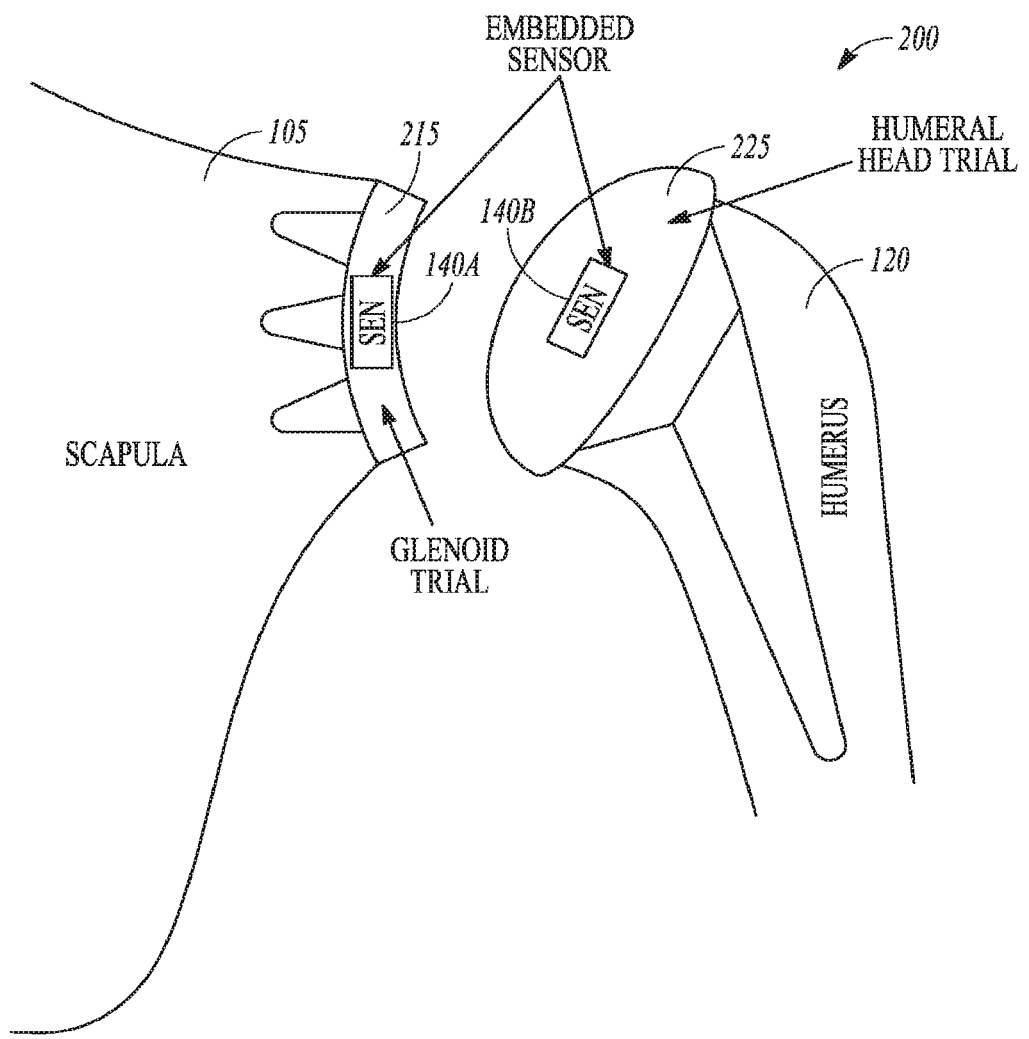
FIG. 2 is a diagram illustrating a total shoulder arthroplasty with sensors embedded in trial prostheses, according to some example embodiments.

FIG. 2 is a diagram illustrating a total shoulder arthroplasty with sensors embedded in trial prostheses, according to some example embodiments. The total shoulder arthroplasty system 200 includes a glenoid trial 215 coupled to the scapula 110 through a glenoid prosthesis. In this example, the glenoid trial 215 includes an embedded force sensor 140A. On the humeral side of the total shoulder arthroplasty system 200, a humeral head trial 225 is added to a humeral prosthesis and includes an embedded force sensor 140B. Like the reverse shoulder arthroplasty system 100, the total shoulder arthroplasty system 200 can optionally include force sensors in only one trial prosthesis or in both as illustrated.

FIGS. 3A and 3B are diagrams illustrating a force sensor module for use within a trial prosthesis, according to some example embodiments. FIG. 3A illustrates the force sensor module 300 in a low force position, or where little to no force is being exerted on the articular surface 310. FIG. 3B illustrates the force sensor module 300 in a high force position, where forces near the design limit are being exerted on the articular surface 310. In this example, the force sensor 300 includes an articular surface 310, a calibrated spring 320, an upper housing 330, a measurement shaft 340, a lower housing 350, and one or more sensors 360. The force sensor module 300 is designed for applications where a joint naturally exhibits some movement or play between articular surfaces of the bones involved by providing a range of motion in the force sensing mechanism. The force sensor 300 functions through a combination of a calibrated spring 320 with a known spring constant and position sensors, such as sensor(s) 360, used to measure the travel of the measurement shaft 340 that defects under loading on the articular surface 310. The sensor(s) 360 can sense position of the shaft through various known technologies, such as magnetic, induction, or magnetostrictive, among others.

Figure 4:
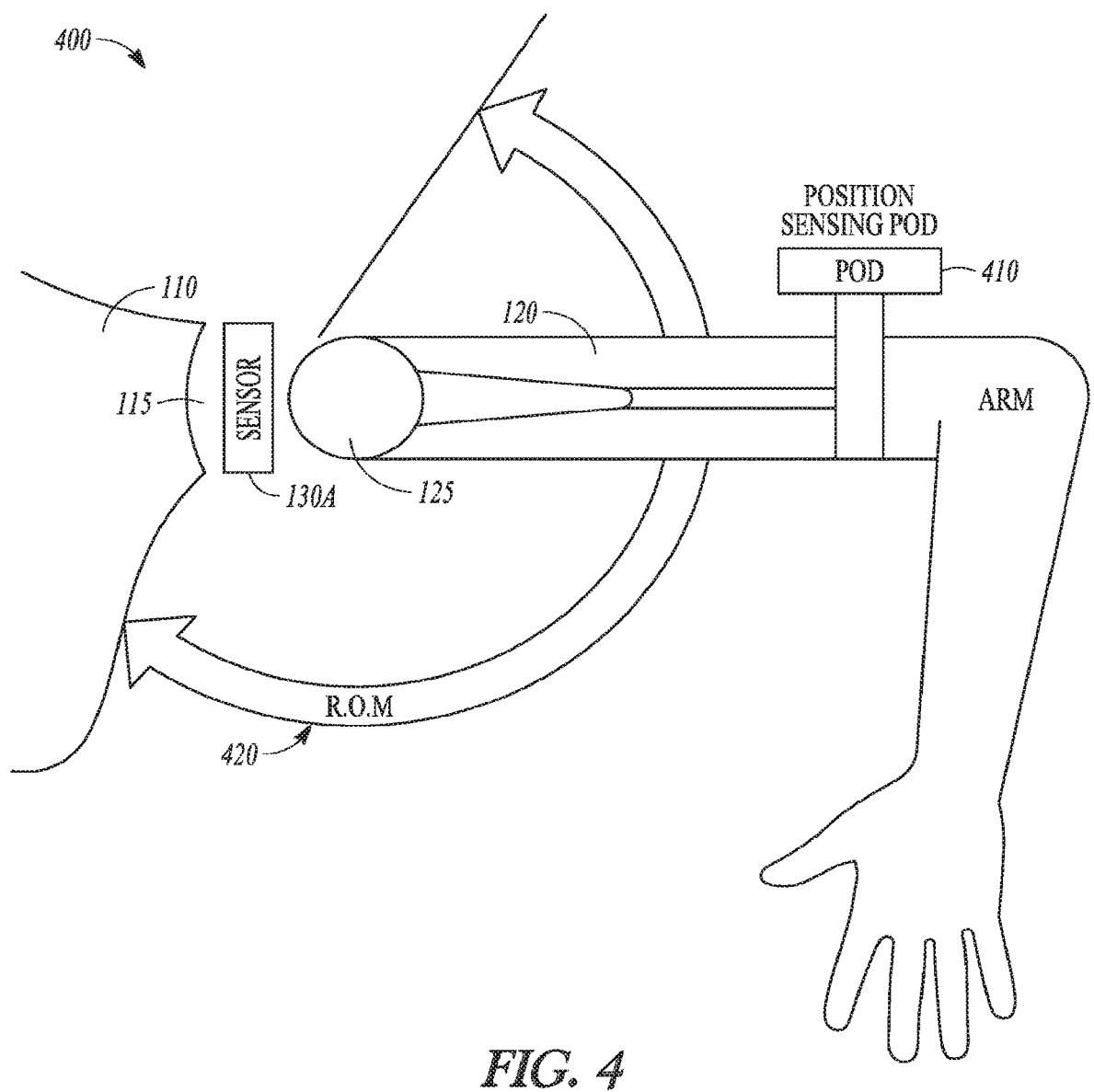
FIG. 4 is a diagram illustrating a positioning sensing module detecting a range of motion of a joint, according to some example embodiments.

FIG. 4 is a diagram illustrating a positioning sensing module detecting a range of motion of a joint, according to some example embodiments. In this example, the range of motion detection system 400 includes a position sensor module 410 shown attached to a humerus 120, which can be moved through a range of motion 420. The range of motion 420 is merely an illustration of the range of motion information the position sensor module 410 can detect. The position sensor module 410 can include a combination of accelerometers, gyroscopes, or similar motion or position sensing technologies. One example of a position sensor module that could be adapted for use in the systems and methods discussed herein is discussed within U.S. Patent Publication 2009/0247863, titled "TRACKING SYSTEM AND METHOD," which is hereby incorporated by reference in its entirety. The position or motion data produced by the position sensor module 410 can be correlated to force sensor data received during the range of motion movements to produce graphical output discussed in detail below.

Figure 5:
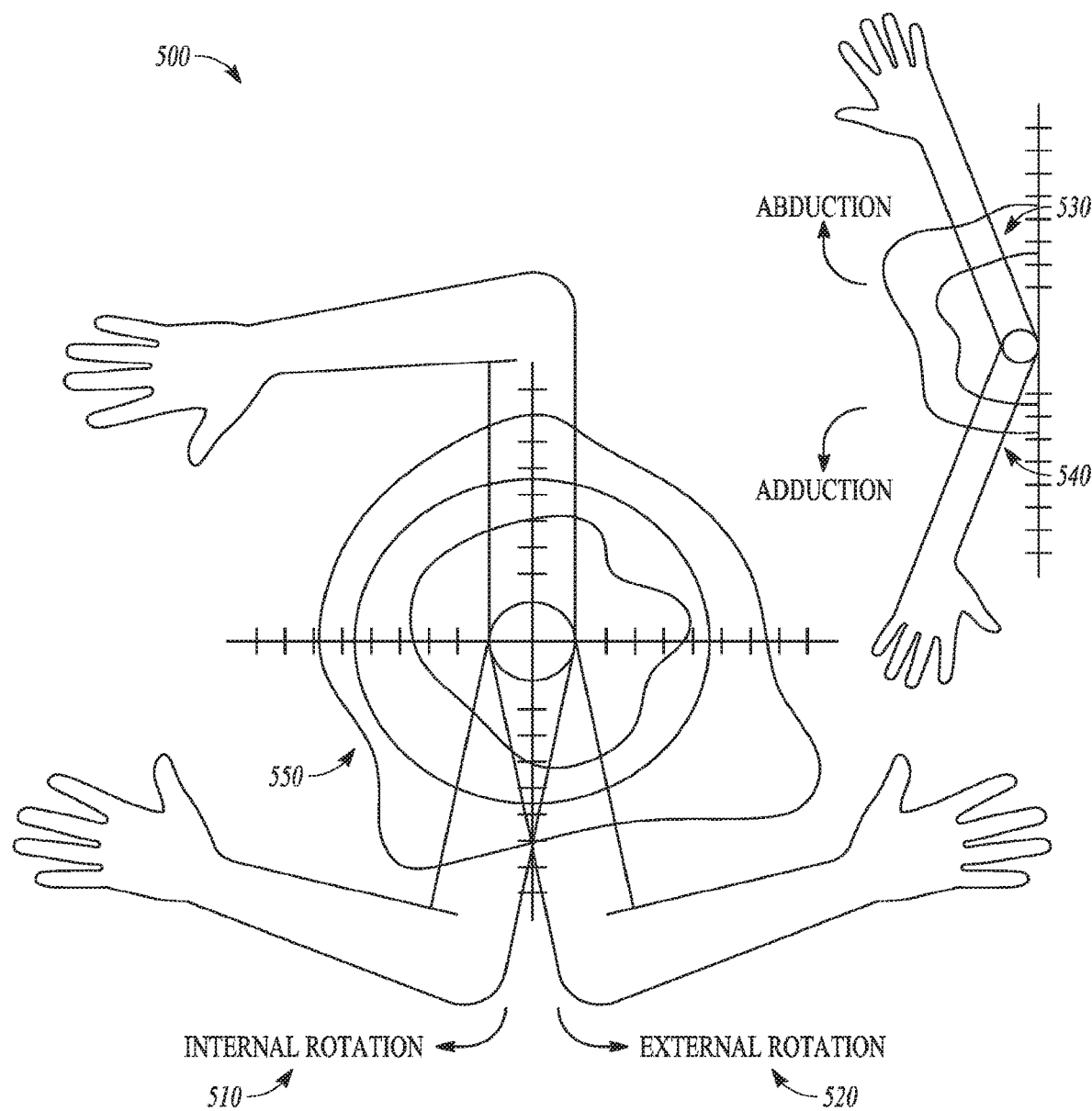
FIG. 5 is a diagram illustrating a graphical range of motion map depicting joint data over a range of motion for the joint, according to some example embodiments.

FIG. 5 is a diagram illustrating a graphical range of motion map depicting joint data over a range of motion for the joint, according to some example embodiments. In an example, the range of motion graph 500 includes an internal rotation axis 510, an external rotation axis 520, an adduction axis 530, an adduction axis 540, and position-based joint data 550. In the illustrated range of motion graph 500, the position-based joint data 550 takes the form of contour lines that can represent joint tension, among other things. In some examples, the position-based joint data 550 is calculated from the force sensor(s) within trial prostheses within the joint collected in conjunction with the position-data.

Figure 6:
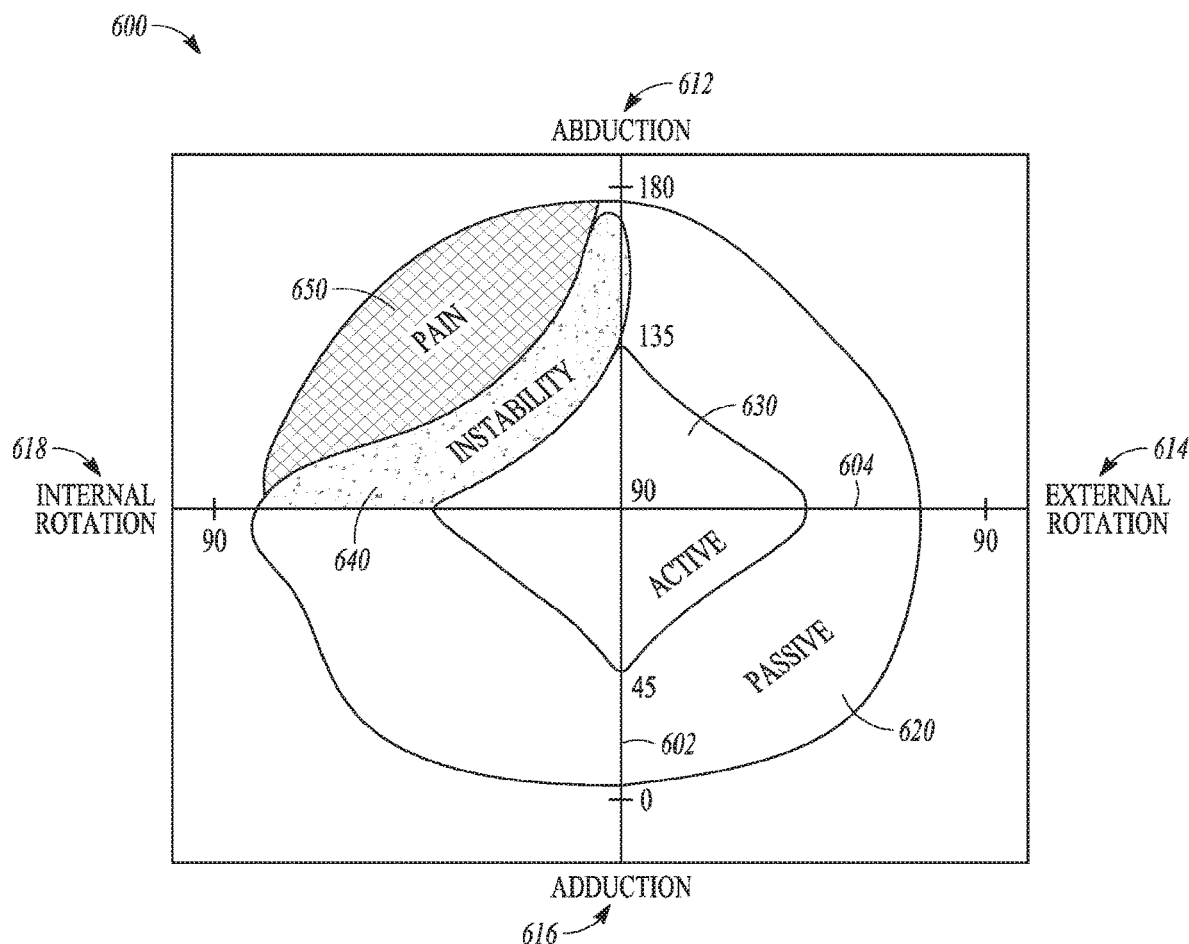
FIG. 6 is a diagram illustration a graphical range of motion map depicting joint data over a range of motion for the joint, according to some example embodiments.

FIG. 6 is a diagram illustration a graphical range of motion map depicting joint data over a range of motion for the joint, according to some example embodiments. In an example, the range of motion graph 600 includes an internal/external rotation axis 602, an abduction/adduction position axis 604, an abduction vector 612, an external rotation vector 614, adduction vector 616, an internal rotation vector 618, a passive range of motion graph 620, an active range of motion graph 630, an instability range of motion graph 640, and a pain range of motion graph 650. The range of motion graph 600 illustrates different options for graphically depicting additional joint data, such as instability and pain. Pain data can be gather from the patient using a feedback input device or verbally. Optionally, the feedback input device includes a series of physical buttons or a computer generated graphical user interface to input pain indications. Instability information can be captured by the surgeon through a similar interface, while the joint is manipulate through a range of motion captured by a position sensor module mounted to the patient. The additional joint data is captured by a computing device and correlated to the position data, which is also captured by the computing device. The computing device can then generate and output numeric data or a graph, such as the range of motion graph 600.

Figure 7:
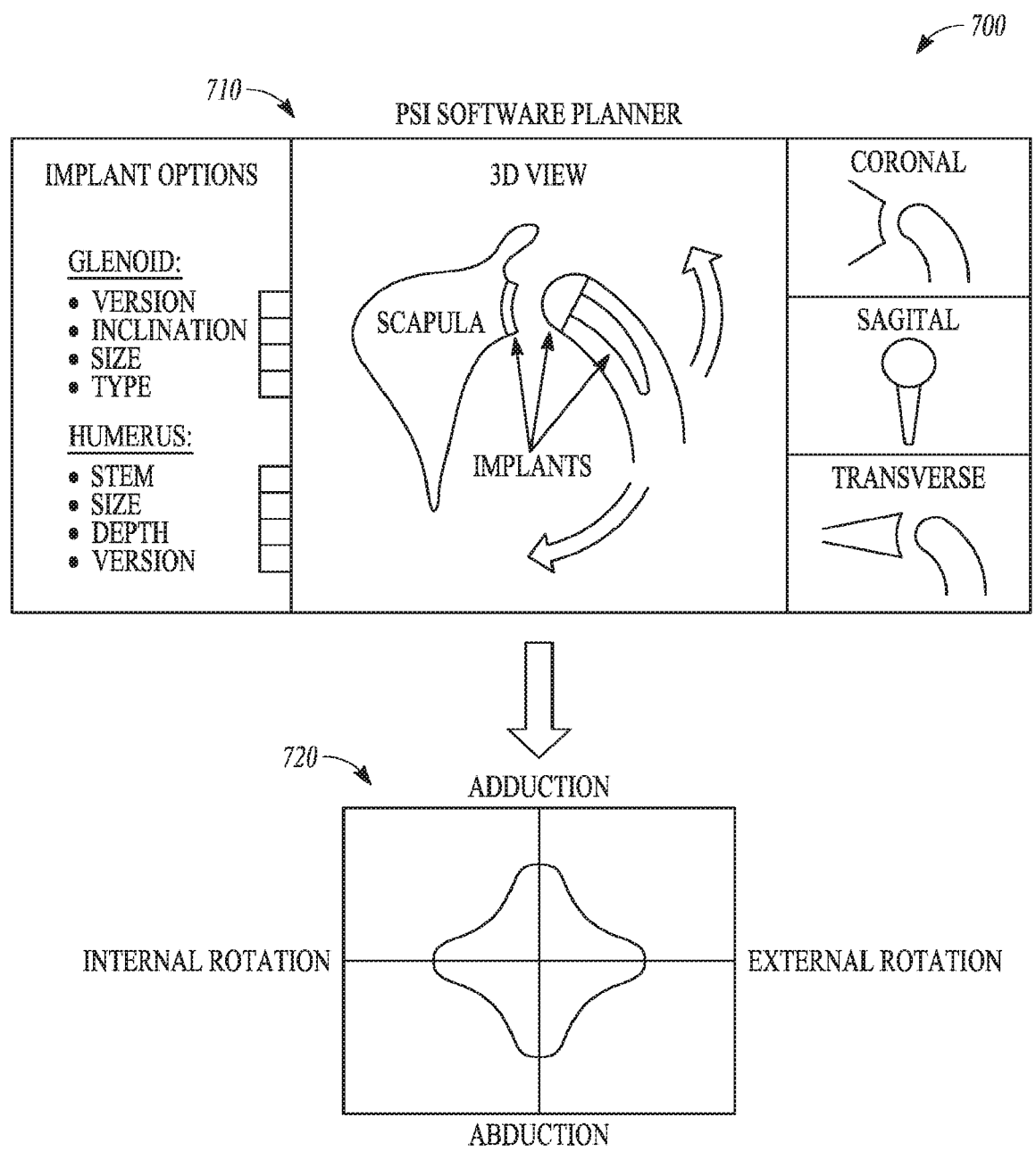
FIG. 7 is a diagram illustrating surgical planning software and graphical output, according to some example embodiments.

FIG. 7 is a diagram illustrating surgical planning software and graphical output, according to some example embodiments. In this example, a surgical planning system 700 includes a surgical planning interface 710 and an example surgical planning output graph 720. The surgical planning system 700 can assist surgeons in planning joint replacement surgeries through use of pre-operative imaging (e.g., CT or MRI). In some examples, the surgical planning system 700 is part of a patient-specific implant system that generates patient-specific cut and alignment guides for use during a joint replacement surgery. The patient-specific instrumentation is modeled based on pre-operative imaging and then manufactured prior to the surgical procedure. In some examples, the surgical planning system 700 provides projections for predicted range of motion given the selected prostheses placement and size. In these examples, the surgical planning system 700 outputs, upon request, a predicted range of motion graph, such as surgical planning output graph 720. The predicted range of motion graph can be used intraoperatively, with the systems and methods discussed herein, to provide quantitative comparison-based feedback to the surgeon during the replacement procedure. Further, the predicted range of motion graph is optionally used to evaluate outcomes post-procedure.

Figure 8A:
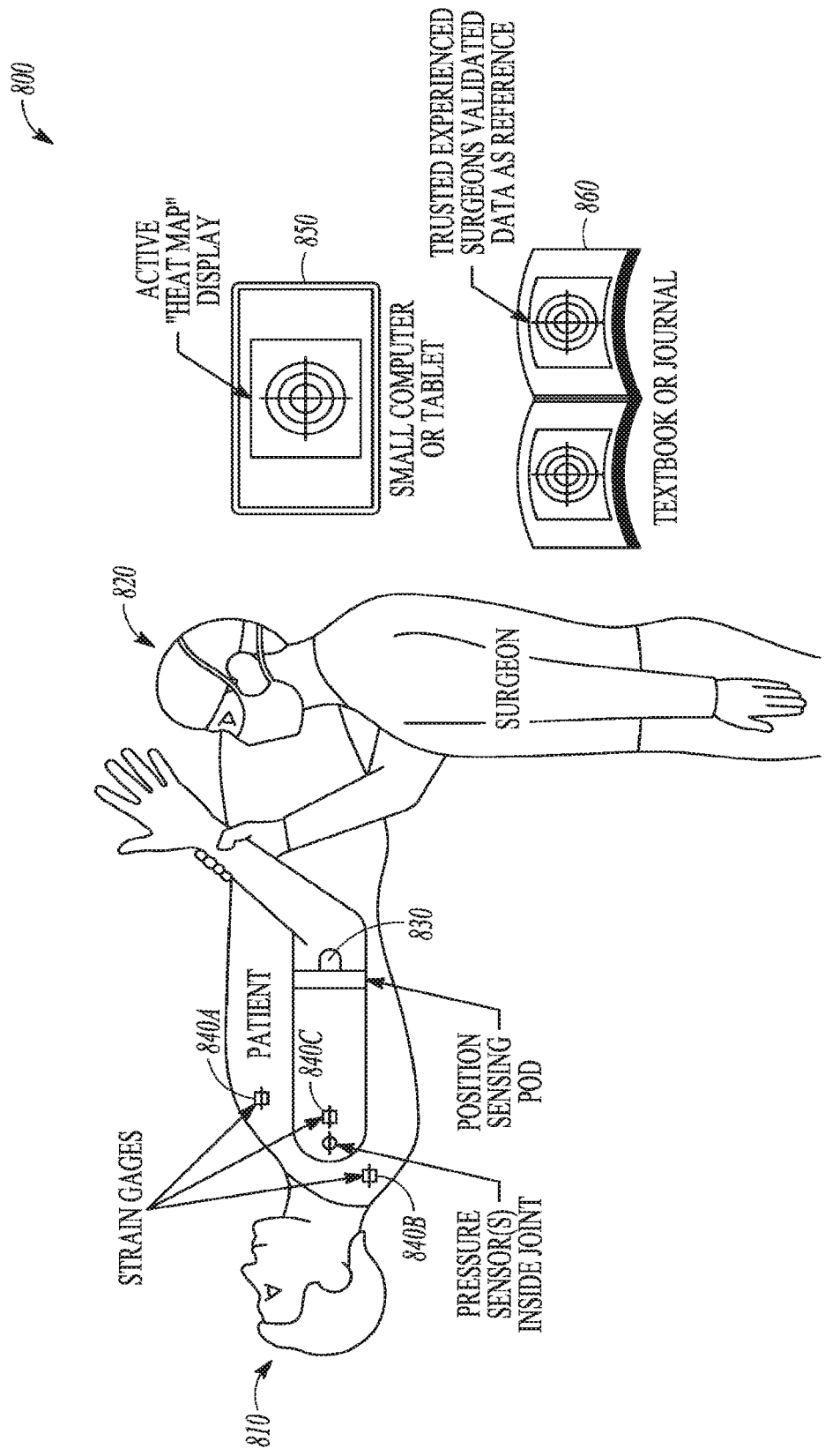
FIG. 8A is a diagram illustrating a sensor-based joint replacement system, according to some example embodiments.

FIG. 8A is a diagram illustrating a sensor-based joint replacement system, according to some example embodiments. In the illustrated example, the sensor-based joint replacement system 800 (or simply sensor-based system 800) includes a position sensor module 830 and strain gauges 840A-840C affixed to patient 810 as well as computing device 850 and procedure standards 860 providing information, as discussed herein, to surgeon 820. Optionally, the procedure standards 860 can be maintained digitally within computing device 850. Further, computing device 850 can optionally analyze input received from force sensors (not shown), strain gauges 840A-840C, and position data from position sensor module 830 in view of the digitally maintained procedure standards 860 to generate further processed output to assist the surgeon in evaluating trial prostheses and other aspects of the joint replacement procedure.

Figure 8B:
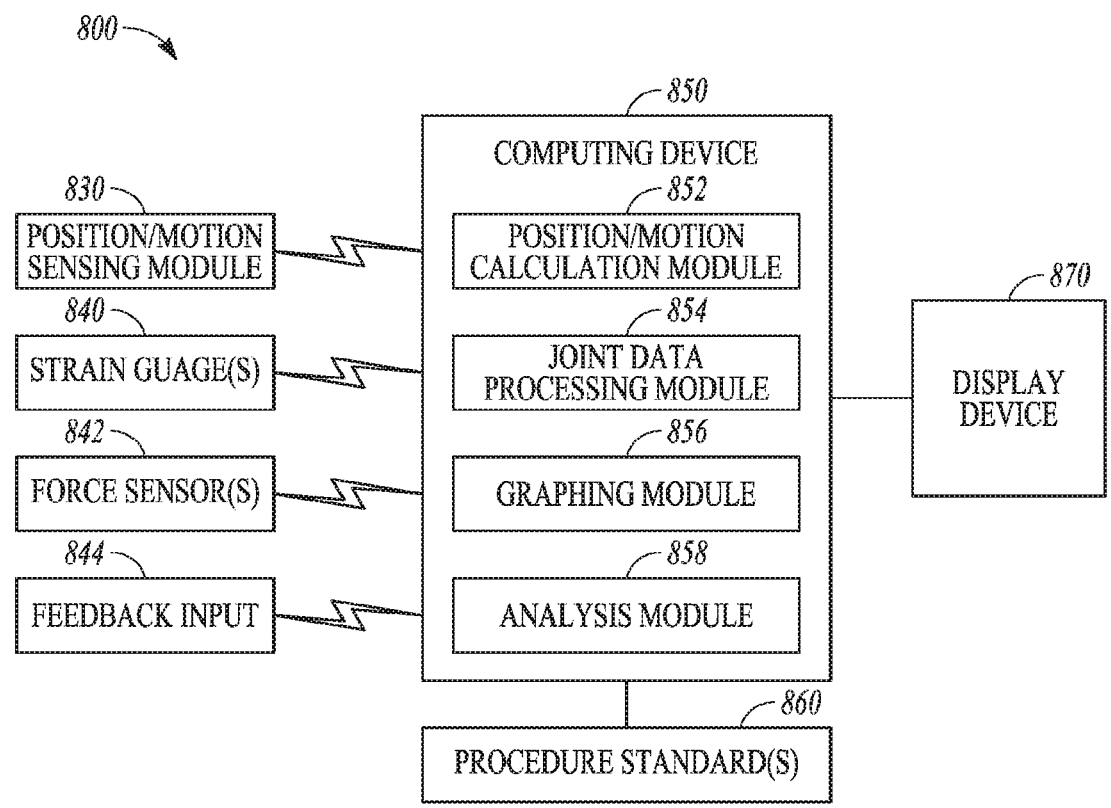
FIG. 8B is a block diagram illustrating a sensor-based joint replacement system, according to some example embodiments.

FIG. 8B is a block diagram illustrating a sensor-based joint replacement system, according to some example embodiments. In this example, the sensor-based system 800 includes position/motion sensing module 830, computing device 850, position/motion calculation module 852, joint data processing module 854, graphing module 856, analysis module 858, procedure standards repository 860, and display device 870. Optionally, sensor-based system 800 includes one or more of strain gauge(s) 840, force sensor(s) 842, and feedback input 844. In this example, the position/motion calculation module 852 receives and processes information from the position/motion sensing module 830. In certain examples, the position/motion calculation module 852 is integrated into the position/motion sensing module 830 and not part of the computing device 850, as illustrated in this example. In some examples, the joint data processing module 854 receives and processes data from strain gauge(s) 840, force sensor(s) 842 and the feedback input 844, depending upon which of these joint data sources are in use and communicating with computing device 850. The joint data process module 854 correlates the received joint data with the position data generated by the position/motion calculation module 852 for use by the graphing module 856. In some examples, the graphing module 856 uses data received from the position/motion calculation module 852 and the joint data processing module 854 to generate range of motion graphs as discussed above. In an example, the analysis module 858 can compare and evaluate output from the graphing module 856 against procedure standards stored in the procedure standard repository 860. Output from the analysis module 858 can be presented to a surgeon via the display device 870 in numeric or graphical form.

Figure 9:
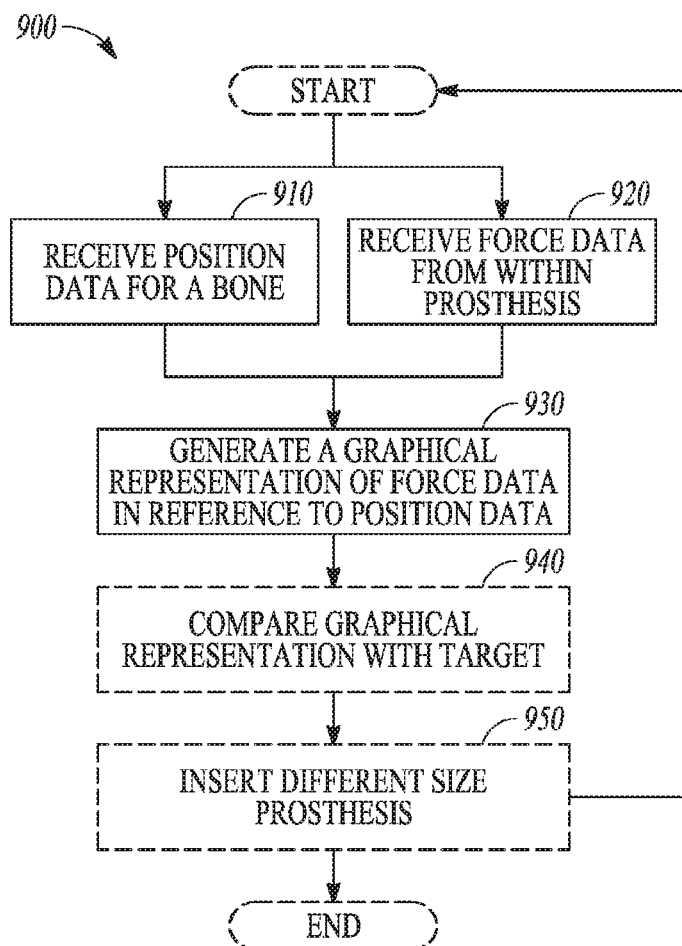
FIG. 9 is a flowchart illustrating a method for providing quantitative feedback during a joint replacement procedure, according to some example embodiments.

FIG. 9 is a flowchart illustrating a method for providing quantitative feedback during a joint replacement procedure, according to some example embodiments. In an example, method 900 includes operations such as receiving position data at 910, concurrently receiving force data from within a prosthesis at 920, generating a graphical representation of force data in reference to position data at 930, and comparing graphical representation with target at 940. Optionally, method 900 further includes comparing graphical representation with target at 940 and inserting different size prosthesis at 950 followed by repeating previous operations.

In an example, the method 900 begins at 910 with the computing device 850 receiving position data for a bone from a position or motion sensor, such as position/motion sensing module 830. At 920, the method 900 concurrent with 910 receives force data from within a prosthesis with computing device 850. Force sensors, such as force sensors 842, can generate force data. At 930, the method 900 continues with the computing device 850 generating a graphical representation of the force data correlated with the position data to generate a range of motion graph, such as range of motion graph 600. Optionally, the method 600 at 930 can include operations that correlate the force data to the position data based on timestamps or similar metadata associated with each data stream (e.g., position data and force data).

Optionally, method 900 continues at 940 with the computing device 850 comparing graphical representation with a target or procedure standard. In some examples, the comparison or evaluation can produce numeric or graphical output representing how close the graphical representation matches to the target, such as a colored heat map illustrating areas of difference and similarity along with relative magnitudes (e.g., red areas indicating high levels of difference and blue areas indicating high levels of similarity). At 950, the method 900 optionally continues with insertion of a different size prosthetic trial and triggering previous operations to re-start after reduction of the joint with the new trial.

Figure 10:
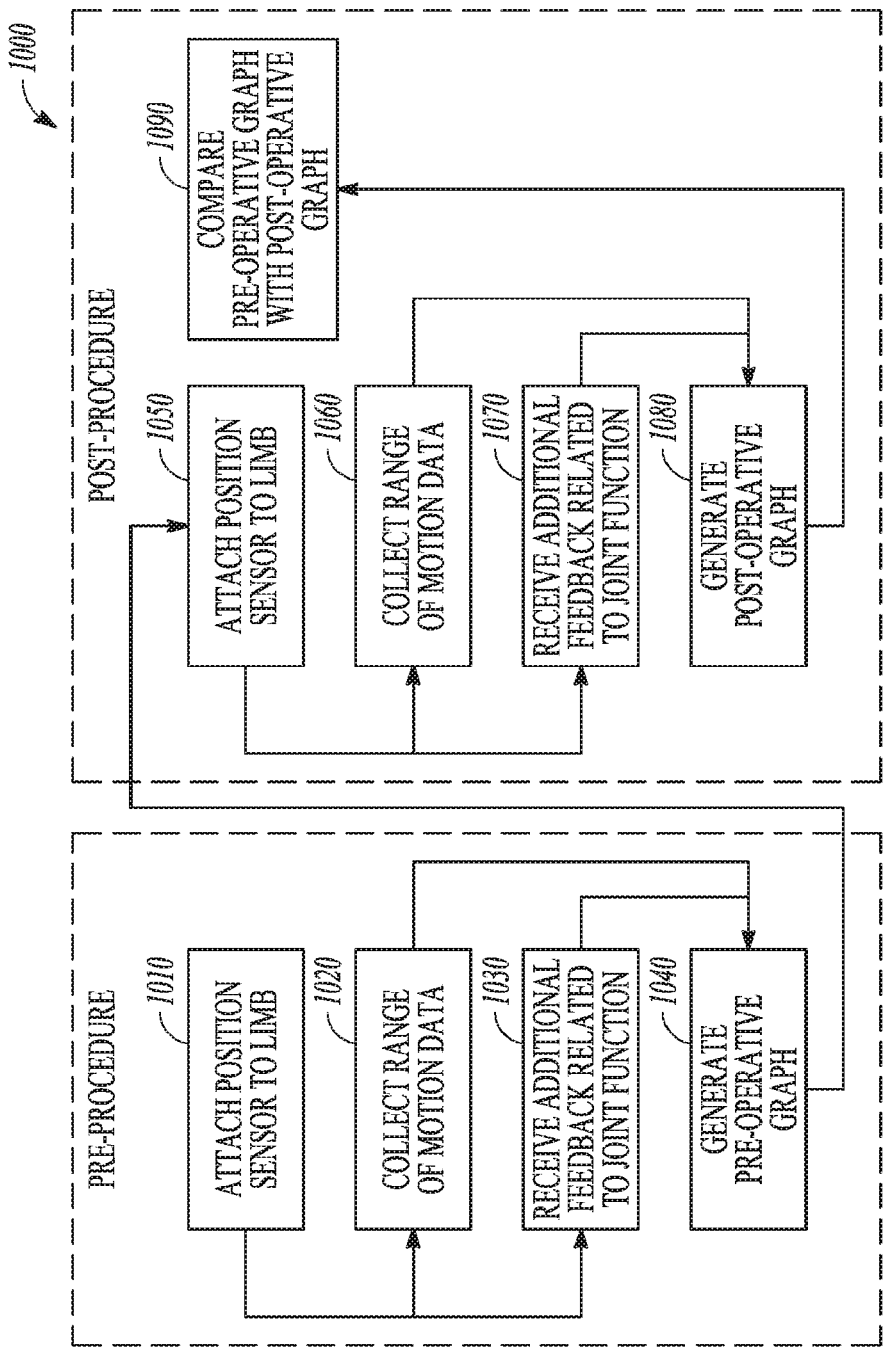
FIG. 10 is a flowchart illustrating a method for quantitative comparison of preoperative and post-operative joint function, according to some example embodiments.

FIG. 10 is a flowchart illustrating a method for quantitative comparison of preoperative and post-operative joint function, according to some example embodiments. In this example, the method 1000 includes operations broken out into two different periods, pre-procedure including operations 1010 through 1040 and post-procedure including operations 1050 through 1090. The pre-procedure operations include attaching a position sensor to a limb at 1010, collecting range of motion data at 1020, concurrently receiving additional feedback related to joint function at 1030, and generating a pre-operative graph at 1040. The post-procedure operations include attaching a position sensor to the limb at 1050, collecting range of motion data at 1060, concurrently receiving additional feedback related to joint function at 1070, generating a post-operative graph at 1080, and comparing the pre-operative graph with the post-operative graph at 1090. In this example, the method 1000 is used to provide quantitative evaluation and feedback of the outcome of a joint replacement procedure. Post-procedure operations can be performed at various time intervals after the joint replacement to further evidence improvements during the healing process.

In an example, the method 1000 begins at 1010 with a position sensor being attached to a limb of a prospective patient. At 1020 and 1030, the method 1000 continues with collection of range of motion data using the position sensor while the limb is actively or passively moved through a range of motion. Active range of motion represents the range of motion attainable by the patient without assistance, while passive range of motion is the range of motion the limb can be moved through with assistance. At 1030, the method 1000, concurrent with operation 1020, continues with feedback (e.g., data) related to joint function being received. In an example, the feedback can include strain gauge information (indicating muscle function or other soft tissue information), instability information, or pain information provided by the patient. Collecting the feedback data concurrently with collecting the range of motion data allows the feedback data to be correlated with the range of motion data. At 1040, the method 1000 continues with the correlated range of motion and feedback data being used to generate a pre-operative graphical representation of joint function. Operations 1010 through 1040 provide quantitative representation of pre-procedure joint function, which can include active versus passive range of motion as well as instability and pain information correlated to position within the range of motion.

The method 1000 can continue with operations 1050 through 1080 repeating operations 1010 through 1040 post-procedure to generating a quantitative representation of post-procedure joint function. At 1090, the method 1000 continues with comparison between the pre-procedure graph and the post-procedure graph to provide quantitative evidence of surgical outcome.

Software Architecture

Figure 11:
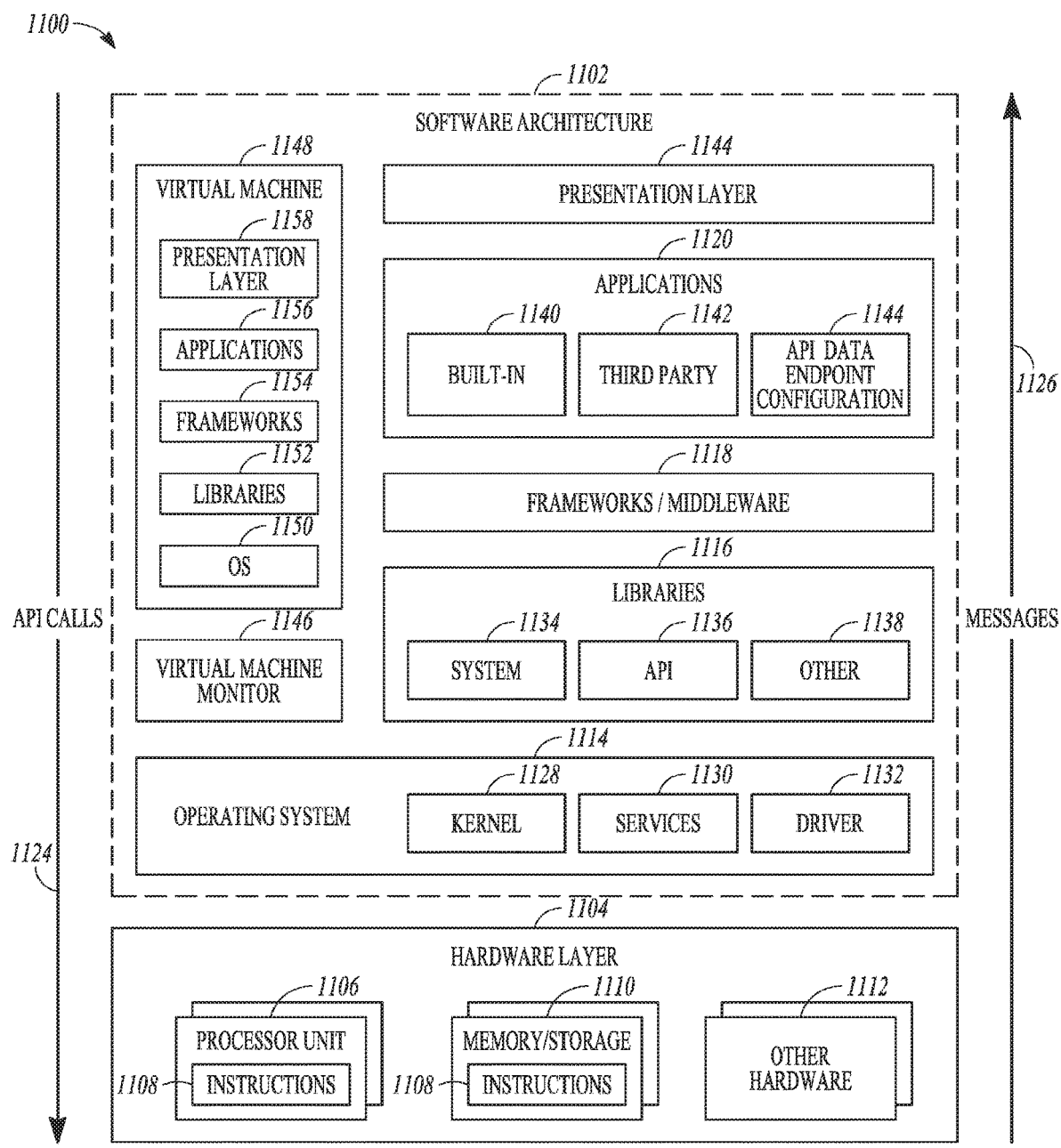
FIG. 11 is a block diagram illustrating an example of a software architecture that may be installed on a machine, according to some example embodiments.

FIG. 11 is a block diagram 1100 illustrating a representative software architecture 1102, which may be used in conjunction with various hardware architectures herein described. FIG. 11 is merely a non-limiting example of a software architecture and it will be appreciated that many other architectures may be implemented to facilitate the functionality described herein. The software architecture 1102 may be executing on hardware such as machine 1200 of FIG. 12 that includes, among other things, processors 1210, memory 1230, and I/O components 1250. A representative hardware layer 1104 is illustrated and can represent, for example, the machine 1200 of FIG. 12. The representative hardware layer 1104 comprises one or more processing units 1106 having associated executable instructions 1108. Executable instructions 1108 represent the executable instructions of the software architecture 1102, including implementation of the methods, modules and so forth of FIGS. 8-10. Hardware layer 1104 also includes memory and/or storage modules 1110, which also have executable instructions 1108. Hardware layer 1104 may also comprise other hardware as indicated by 1112 which represents any other hardware of the hardware layer 1104, such as the other hardware illustrated as part of machine 1200.

In the example architecture of FIG. 11, the software 1102 may be conceptualized as a stack of layers where each layer provides particular functionality. For example, the software 1102 may include layers such as an operating system 1114, libraries 1116, frameworks/middleware 1118, applications 1120 and presentation layer 1122. Operationally, the applications 1120 and/or other components within the layers may invoke application programming interface (API) calls 1124 through the software stack and receive a response, returned values, and so forth illustrated as messages 1126 in response to the API calls 1124. The layers illustrated are representative in nature and not all software architectures have all layers. For example, some mobile or special purpose operating systems may not provide a frameworks/middleware layer 1118, while others may provide such a layer. Other software architectures may include additional or different layers.

The operating system 1114 may manage hardware resources and provide common services. The operating system 1114 may include, for example, a kernel 1128, services 1130, and drivers 1132. The kernel 1128 may act as an abstraction layer between the hardware and the other software layers. For example, the kernel 1128 may be responsible for memory management, processor management (e.g., scheduling), component management, networking, security settings, and so on. The services 1130 may provide other common services for the other software layers. The drivers 1132 may be responsible for controlling or interfacing with the underlying hardware. For instance, the drivers 1132 may include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1116 may provide a common infrastructure that may be utilized by the applications 1120 and/or other components and/or layers. The libraries 1116 typically provide functionality that allows other software modules to perform tasks in an easier fashion than to interface directly with the underlying operating system 1114 functionality (e.g., kernel 1128, services 1130 and/or drivers 1132). The libraries 1116 may include system 1134 libraries (e.g., C standard library) that may provide functions such as memory allocation functions, string manipulation functions, mathematic functions, and the like. In addition, the libraries 1116 may include API libraries 1136 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 1116 may also include a wide variety of other libraries 1138 to provide many other APIs to the applications 1120 and other software components/modules.

The frameworks 1118 (also sometimes referred to as middleware) may provide a higher-level common infrastructure that may be utilized by the applications 1120 and/or other software components/modules. For example, the frameworks 1118 may provide various graphic user interface (GUI) functions, high-level resource management, high-level location services, and so forth. The frameworks 1118 may provide a broad spectrum of other APIs that may be utilized by the applications 1120 and/or other software components/modules, some of which may be specific to a particular operating system or platform.

The applications 1120 includes built-in applications 1140 and/or third party applications 1142. Examples of representative built-in applications 1140 may include, but are not limited to, a contacts application, a browser application, a book reader application, a location application, a media application, a messaging application, and/or a game application. Third party applications 1142 may include any of the built in applications as well as a broad assortment of other applications. In a specific example, the third party application 1142 (e.g., an application developed using the Android™ or iOS™ software development kit (SDK) by an entity other than the vendor of the particular platform) may be mobile software running on a mobile operating system such as iOS™, Android™, Windows® Phone, or other mobile operating systems. In this example, the third party application 1142 may invoke the API calls 1124 provided by the mobile operating system such as operating system 1114 to facilitate functionality described herein.

The applications 1120 may utilize built in operating system functions (e.g., kernel 1128, services 1130 and/or drivers 1132), libraries (e.g., system 1134, APIs 1136, and other libraries 1138), frameworks/middleware 1118 to create user interfaces to interact with users of the system. Alternatively, or additionally, in some systems interactions with a user may occur through a presentation layer, such as presentation layer 1144. In these systems, the application/module "logic" can be separated from the aspects of the application/module that interact with a user.

Some software architectures utilize virtual machines. In the example of FIG. 11, this is illustrated by virtual machine 1148. A virtual machine creates a software environment where applications/modules can execute as if they were executing on a hardware machine (such as the machine of FIG. 12, for example). A virtual machine is hosted by a host operating system (operating system 1114 in FIG. 12) and typically, although not always, has a virtual machine monitor 1146, which manages the operation of the virtual machine as well as the interface with the host operating system (i.e., operating system 1114). A software architecture executes within the virtual machine such as an operating system 1150, libraries 1152, frameworks/middleware 1154, applications 1156 and/or presentation layer 1158. These layers of software architecture executing within the virtual machine 1148 can be the same as corresponding layers previously described or may be different.

Example Machine Architecture and Machine-Readable Medium

Figure 12:
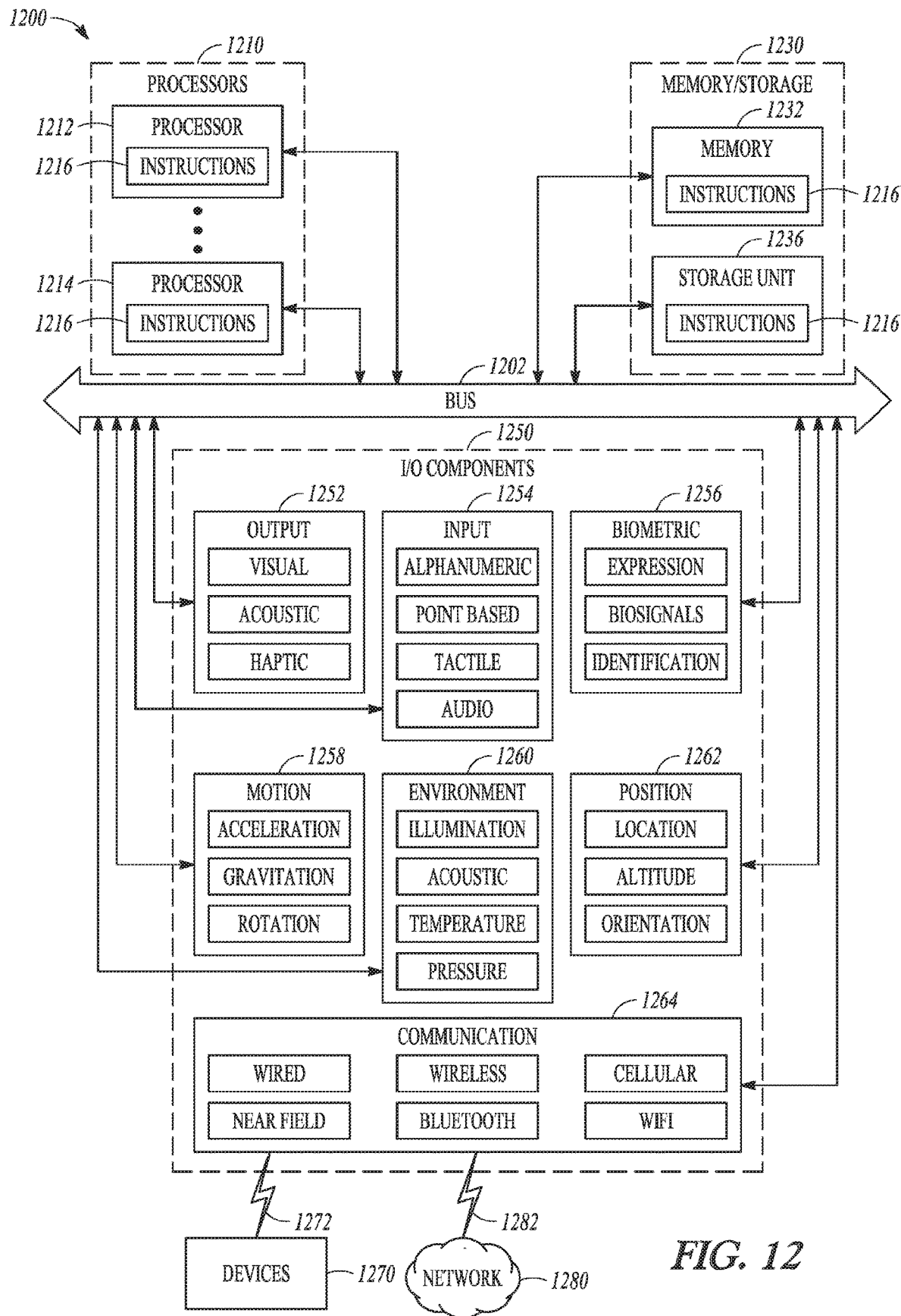
FIG. 12 illustrates a diagrammatic representation of a machine in the form of a computer system within which a set of instructions may be executed for causing the machine to perform any one or more of the methodologies discussed herein, according to an example embodiment.
Figure 13:
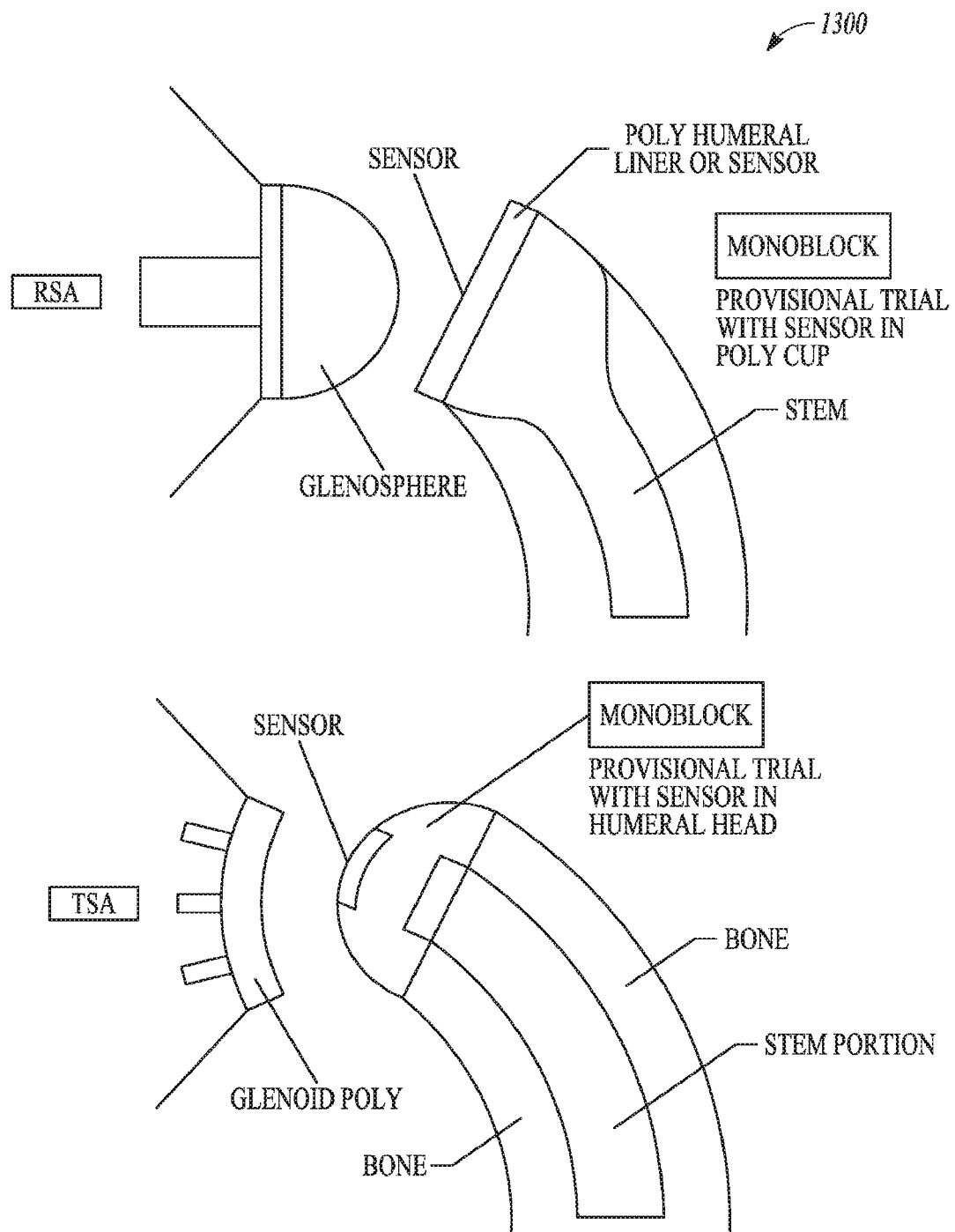
FIG. 13 is a diagram illustrating a reverse shoulder arthroplasty and total shoulder arthroplasty monoblock provisional trial components with sensors embedded, according to some example embodiments.
Figure 14:
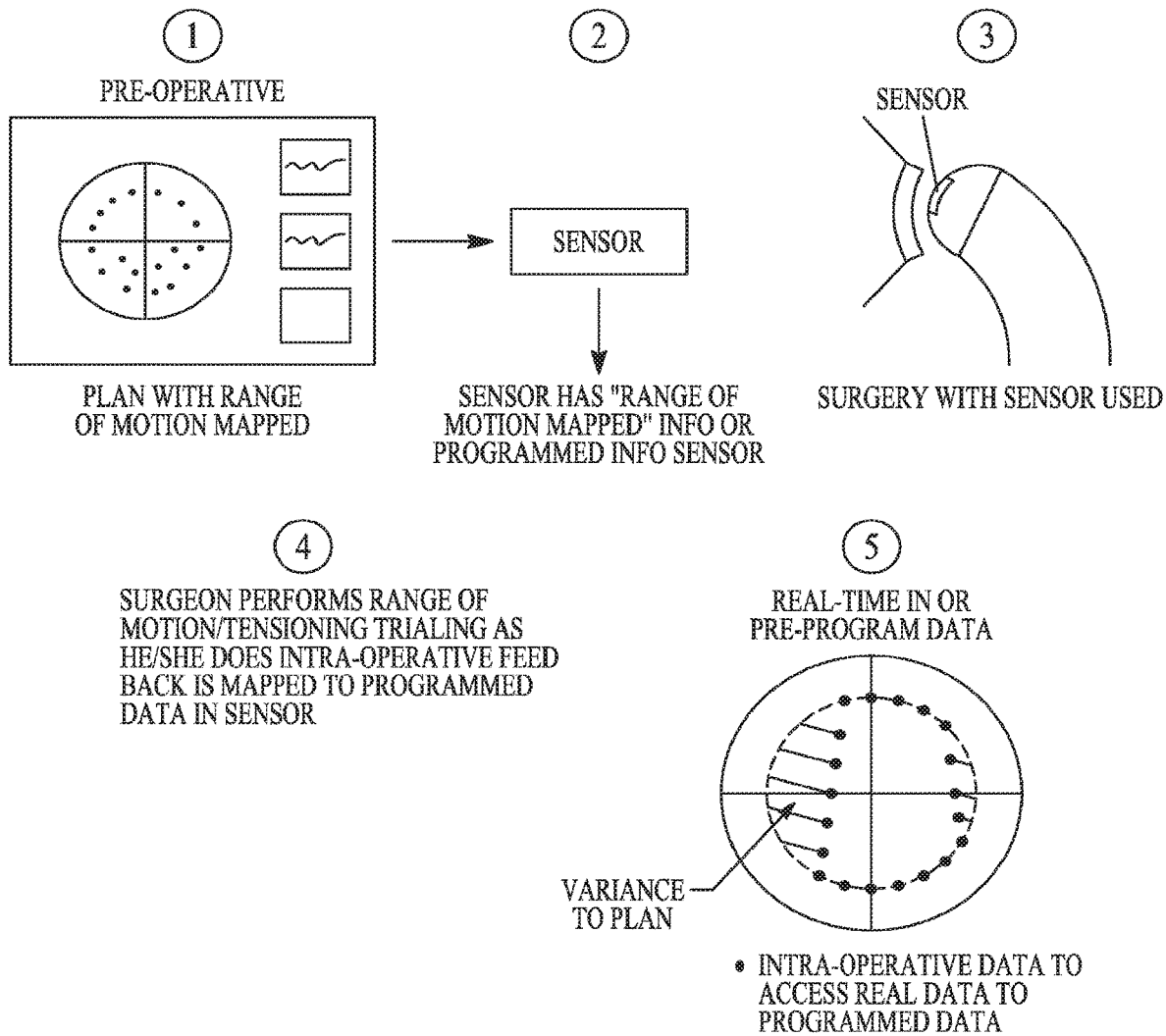
FIG. 14 is a diagram illustrating a method for pre-operative through intra-operative use of force sensor and quantitative mapping, according to some example embodiments.

FIG. 12 is a block diagram illustrating components of a machine 1200, according to some example embodiments, able to read instructions from a machine-readable medium (e.g., a machine-readable storage medium) and perform any one or more of the methodologies discussed herein. Specifically, FIG. 12 shows a diagrammatic representation of the machine 1200 in the example form of a computer system, within which instructions 1216 (e.g., software, a program, an application, an applet, an app, or other executable code) for causing the machine 1200 to perform any one or more of the methodologies discussed herein may be executed. For example the instructions may cause the machine to execute the flow diagrams of FIGS. 9 and 10. Additionally, or alternatively, the instructions may implement modules 852-858 of FIG. 8B, and so forth. The instructions transform the general, non-programmed machine into a particular machine programmed to carry out the described and illustrated functions in the manner described. In alternative embodiments, the machine 1200 operates as a standalone device or may be coupled (e.g., networked) to other machines. In a networked deployment, the machine 1200 may operate in the capacity of a server machine or a client machine in a server-client network environment, or as a peer machine in a peer-to-peer (or distributed) network environment. The machine 1200 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), or any machine capable of executing the instructions 1216, sequentially or otherwise, that specify actions to be taken by machine 1200. Further, while only a single machine 1200 is illustrated, the term "machine" shall also be taken to include a collection of machines 1200 that individually or jointly execute the instructions 1216 to perform any one or more of the methodologies discussed herein.

The machine 1200 may include processors 1210, memory 1230, and I/O components 1250, which may be configured to communicate with each other such as via a bus 1202. In an example embodiment, the processors 1210 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, processor 1212 and processor 1214 that may execute instructions 1216. The term "processor" is intended to include multi-core processor that may comprise two or more independent processors (sometimes referred to as "cores") that may execute instructions contemporaneously. Although FIG. 12 shows multiple processors, the machine 1200 may include a single processor with a single core, a single processor with multiple cores (e.g., a multi-core process), multiple processors with a single core, multiple processors with multiples cores, or any combination thereof.

The memory/storage 1230 may include a memory 1232, such as a main memory, or other memory storage, and a storage unit 1236, both accessible to the processors 1210 such as via the bus 1202. The storage unit 1236 and memory 1232 store the instructions 1216 embodying any one or more of the methodologies or functions described herein. The instructions 1216 may also reside, completely or partially, within the memory 1232, within the storage unit 1236, within at least one of the processors 1210 (e.g., within the processor's cache memory), or any suitable combination thereof, during execution thereof by the machine 1200. Accordingly, the memory 1232, the storage unit 1236, and the memory of processors 1210 are examples of machine-readable media.

As used herein, "machine-readable medium" means a device able to store instructions and data temporarily or permanently and may include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 1216. The term "machine-readable medium" shall also be taken to include any medium, or combination of multiple media, that is capable of storing instructions (e.g., instructions 1216) for execution by a machine (e.g., machine 1200), such that the instructions, when executed by one or more processors of the machine 1200 (e.g., processors 1210), cause the machine 1200 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 1250 may include a wide variety of components to receive input, provide output, produce output, transmit information, exchange information, capture measurements, and so on. The specific I/O components 1250 that are included in a particular machine will depend on the type of machine. For example, portable machines such as mobile phones will likely include a touch input device or other such input mechanisms, while a headless server machine will likely not include such a touch input device. It will be appreciated that the I/O components 1250 may include many other components that are not shown in FIG. 12. The I/O components 1250 are grouped according to functionality merely for simplifying the following discussion and the grouping is in no way limiting. In various example embodiments, the I/O components 1250 may include output components 1252 and input components 1254. The output components 1252 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1254 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1250 may include biometric components 1256, motion components 1258, environmental components 1260, or position components 1262 among a wide array of other components. For example, the biometric components 1256 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1258 may include acceleration sensor components (e.g., accelerometer), gravitation sensor components, rotation sensor components (e.g., gyroscope), and so forth. The environmental components 1260 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1262 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1250 may include communication components 1264 operable to couple the machine 1200 to a network 1280 or devices 1270 via coupling 1282 and coupling 1272 respectively. For example, the communication components 1264 may include a network interface component or other suitable device to interface with the network 1280. In further examples, communication components 1264 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1270 may be another machine or any of a wide variety of peripheral devices (e.g., a peripheral device coupled via a Universal Serial Bus (USB)).

Moreover, the communication components 1264 may detect identifiers or include components operable to detect identifiers. For example, the communication components 1264 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1264, such as, location via Internet Protocol (IP) geo-location, location via Wi-Fi® signal triangulation, location via detecting a NFC beacon signal that may indicate a particular location, and so forth.

Transmission Medium

In various example embodiments, one or more portions of the network 1280 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 1280 or a portion of the network 1280 may include a wireless or cellular network and the coupling 1282 may be a Code Division Multiple Access (CDMA) connection, a Global System for Mobile communications (GSM) connection, or other type of cellular or wireless coupling. In this example, the coupling 1282 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The instructions 1216 may be transmitted or received over the network 1280 using a transmission medium via a network interface device (e.g., a network interface component included in the communication components 1264) and utilizing any one of a number of well-known transfer protocols (e.g., hypertext transfer protocol (HTTP)). Similarly, the instructions 1216 may be transmitted or received using a transmission medium via the coupling 1272 (e.g., a peer-to-peer coupling) to devices 1270. The term "transmission medium" shall be taken to include any intangible medium that is capable of storing, encoding, or carrying instructions 1216 for execution by the machine 1200, and includes digital or analog communications signals or other intangible medium to facilitate communication of such software.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

VARIOUS NOTES & EXAMPLES

Each of these non-limiting examples can stand on its own, or can be combined in various permutations or combinations with one or more of the other examples.

Example 1 describes subject matter that can include a method providing graphical feedback visualizing forces within a joint through a range of motion of the joint. The method can comprise receiving position data, receiving force data, and generating a graphical representation based on the position data and the force data. The receiving position data can include data for at least one bone of a joint while the at least one bone is moved through a range of motion (ROM). The receiving force data can occur concurrently to receiving the position data and usings one or more processors, the force data can be collected from at least one force sensor embedded within a trial prosthesis in the joint. The graphical representation can illustrate changes in the force data versus locations of the bone as it moved through the ROM.

In Example 2, the subject matter of Example 1 can optionally include concurrently to receiving the position data, receiving strain gauge data from one or more strain gauges attached to one or more body parts adjacent the joint.

In Example 3, the subject matter of Example 2 can optionally include measuring muscle activation with the strain gauge.

In Example 4, the subject matter of any one of Examples 1 to 3 can optionally include comparing the graphical representation with pre-generated target graphical presentation to determine whether the trial prosthesis provides target joint tension throughout the range of motion.

In Example 5, the subject matter of any one of Examples 1 to 4 can optionally include receiving the position data including receiving position data provided by one or more sensors removably coupled the at least one bone.

In Example 6, the subject matter of Example 5 can optionally include
 the one or more sensors being at least one of an accelerometer and a gyroscope.

In Example 7, the subject matter of any one of Examples 1 to 6 can optionally include the force data being received from a single force sensor embedded within a central portion of the trial prosthesis.

In Example 8, the subject matter of any one of Examples 1 to 6 can optionally include the force data is received from multiple force sensors embedded within the trial prosthesis.

In Example 9, the subject matter of Example 8 can optionally include force data that includes data representative of different areas of the trial prosthesis.

In Example 10, the subject matter of any one of Examples 8 or 9 can optionally include the trial prosthesis being semi-hemispherical and the multiple force sensors including a first sensor receiving force data from the base of the semi-hemispherical shape and multiple additional sensors around a perimeter of the semi-hemispherical shape.

In Example 11, the subject matter of any one of Examples 1 to 7 can optionally include the trial prosthesis including a set of inserts of different sizes, wherein each insert of the set of insert includes at least one force sensor.

In Example 12, the subject matter of Example 1 can optionally include the trial prosthesis including an insert fitted with a sensor module to generate force data representative of the tension within the joint.

In Example 13, the subject matter of Example 12 can optionally include the insert including an articular surface to engage a mating articular surface on a second prosthesis or native bone of the joint.

In Example 14, the subject matter of Example 12 can optionally include the insert with a piston portion that compresses in response to forces exerted on at least a portion of an articular surface.

In Example 15, the subject matter of Example 14 can optionally include the force data being received from a sensor module detecting movements in the piston portion.

In Example 16, the subject matter of Example 14 can optionally include the piston portion with a spring to keep the articular surface engaged with a mating articular surface on a second prosthesis or native bone of the joint.

Example 17 describes subject matter that can include a method to quantify range of motion improvements after a joint replacement procedure. The method can comprise attaching a position sensor, collecting a first set of range of motion data, receiving additional feedback, generating a pre-operative graph, re-performing similar operations post joint replacement, and comparing the pre-operative graph to the post-operative graph. The method includes operations prior to joint replacement and post joint replacement to allow for objective comparison of range of motion. Attaching the position sensor module to the limb to capture range of motion information for the joint. The collecting a first set of range of motion data corresponds to movement of the limb associated with the joint. Receiving the additional feedback can is performed concurrently with collecting the range of motion data, and is related to joint function to generate a first set of feedback data. Generating the pre-operative graph includes the first set of range of motion data and the first set of feedback data correlated to the range of motion data. Subsequent to the joint replacement procedure, the method includes attaching the position sensor module, collecting range of motion data, receiving additional feedback and generating a post-operative graph. Further, the method includes comparing the pre-operative graph to the post-operative graph to determine quantitative results related to the joint replacement procedure.

In Example 18, the subject matter of Example 17 can optionally include collecting range of motion data with collecting active range of motion data reflective of unassisted limb movement.

In Example 19, the subject matter of Example 18 can optionally include the first set of range of motion data and the second set of range of motion data including the active range of motion data.

In Example 20, the subject matter of any one of Examples 17 to 19 can optionally include collecting range of motion data includes collecting passive range of motion data reflective of assisted limb movement.

In Example 21, the subject matter of Example 20 can optionally include the first set of range of motion data and the second set of range of motion date include the passive range of motion data.

In Example 22, the subject matter of any one of Examples 17 to 21 can optionally include receiving the additional feedback includes receiving feedback related to joint instability.

In Example 23, the subject matter of any one of Examples 17 to 22 can optionally include receiving the additional feedback includes receiving pain information.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less The claimed invention includes:

1. A sensor device for use within a joint prosthesis, the sensor device comprising:
   a measurement shaft coupled to an articular surface component of the joint prosthesis;
   a bias element biasing the measurement shaft into a first unloaded position;
   a housing containing the measurement shaft and bias element; and
   a position sensor affixed within the housing to detect a position of the measurement shaft relative to the housing,
   wherein the bias element is a coil spring surrounding the measurement shaft.

2. The sensor device of claim 1, wherein the coil spring is calibrated to enable translation of deflection distance into a force measurement to be output by the sensor device.

3. The sensor device of claim 1, wherein the housing includes an upper housing comprising a cylindrical body dimensioned to contain the measurement shaft and the coil spring.

4. The sensor device of claim 3, wherein the housing includes a lower housing comprising a second cylindrical body coupled to the upper housing and interconnected by a bore dimensioned to receive a measurement end of the measurement shaft.

5. The sensor device of claim 4, wherein the lower housing includes the position sensor disposed along at least one side portion of the second cylindrical body.

6. The sensor device of claim 1, wherein the position sensor is a magnetic position sensor.

7. The sensor device of claim 1, wherein the position sensor is an induction sensor.

8. The sensor device of claim 1, wherein the position sensor is a magnetostrictive sensor.

9. An instrumented trial joint prosthesis system comprising:
   a joint prosthesis including an implantable body and an articular component moveable relative to the implantable body, wherein the articular component includes an articular surface opposite the implantable body;
   a sensor module disposed within the implantable body and coupled to the articular component, the sensor module comprising:
   a measurement shaft coupled to the articular component of the joint prosthesis;
   a bias element biasing the measurement shaft into a first unloaded position;
   a housing embedded within the implantable body, the housing containing the measurement shaft and bias element; and
   a position sensor affixed within the housing in a position to detect a position of the measurement shaft.

10. The instrumented trial joint prosthesis system of claim 9, wherein the articular component and the measurement shaft include a range of travel from the first unloaded position to a second maximum load position and the position sensor is configured to detect positions of the measurement shaft from the first unloaded position to the second maximum load position.

11. The instrumented trial joint prosthesis system of claim 10, wherein in the second maximum load position a portion of the articular component abuts the implantable body.

12. The instrumented trial joint prosthesis system of claim 10, wherein in the first unloaded position the articular component is spaced a distance from the implantable body.

13. The instrumented trial joint prosthesis system of claim 9, wherein the bias element is a calibrated coil spring to enable translation of deflection distance into a force measurement to be output by the sensor module.

14. The instrumented trial joint prosthesis system of claim 13, wherein the housing includes an upper housing comprising a cylindrical body dimensioned to contain the measurement shaft and the coil spring.

15. The instrumented trial joint prosthesis system of claim 14, wherein the housing includes a lower housing comprising a second cylindrical body coupled to the upper housing and interconnected by a bore dimensioned to receive a measurement end of the measurement shaft.

16. The instrumented trial joint prosthesis system of claim 9, wherein the position sensor is selected from a group of sensors including:
   a magnetic position sensor;
   a induction position sensor; and
   a magnetostrictive position sensor.

17. A trial shoulder joint prosthesis comprising:
   a humeral articular component configured to slidably engage a glenoid articular surface;
   a humeral stem implant movably coupled to the humeral articular component and configured to be inserted into a humerus bone of a patient;
   a sensor module coupled between the humeral articular component and the humeral stem implant, the sensor module comprising:
   a measurement shaft coupled to the humeral articular component;
   a calibrated coil spring biasing the measurement shaft into a first position, wherein in the first position the humeral articular component is engaged with the glenoid articular surface when the trial shoulder joint prosthesis is implanted in the patient;
   a housing containing the measurement shaft and the calibrated coil spring; and
   a position sensor affixed within the housing in a position to detect a position of the measurement shaft.

18. The trial shoulder joint prosthesis of claim 17, wherein the humeral articular component includes a humeral tray trial configured to engage a glenosphere.

19. The trial shoulder joint prosthesis of claim 17, wherein the humeral articular component includes a humeral head trial configured to engage a glenoid trial.

20. A sensor device for use within a joint prosthesis, the sensor device comprising:
   a measurement shaft coupled to an articular surface component of the joint prosthesis;
   a bias element biasing the measurement shaft into a first unloaded position;
   a housing containing the measurement shaft and bias element; and
   a position sensor affixed within the housing to detect a position of the measurement shaft relative to the housing,
   wherein the position sensor is a magnetic position sensor.

21. A sensor device for use within a joint prosthesis, the sensor device comprising:
- a measurement shaft coupled to an articular surface component of the joint prosthesis;
- a bias element biasing the measurement shaft into a first unloaded position;
- a housing containing the measurement shaft and bias element; and
- a position sensor affixed within the housing to detect a position of the measurement shaft relative to the housing, wherein the position sensor is an induction sensor.

22. A sensor device for use within a joint prosthesis, the sensor device comprising:
- a measurement shaft coupled to an articular surface component of the joint prosthesis;
- a bias element biasing the measurement shaft into a first unloaded position;
- a housing containing the measurement shaft and bias element; and
- a position sensor affixed within the housing to detect a position of the measurement shaft relative to the housing, wherein the position sensor is a magnetostrictive sensor.

* * * * *